(12) United States Patent
Ogi et al.

(10) Patent No.: US 8,438,912 B2
(45) Date of Patent: May 14, 2013

(54) DETECTION DEVICE

(75) Inventors: Hirotsugu Ogi, Hirakata (JP); Fumihito Kato, Settsu (JP); Masahiko Hirao, Toyono-gun (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 0 days.

(21) Appl. No.: 13/519,045

(22) PCT Filed: Dec. 9, 2010

(86) PCT No.: PCT/JP2010/072163
§ 371 (c)(1),
(2), (4) Date: Jun. 25, 2012

(87) PCT Pub. No.: WO2011/121859
PCT Pub. Date: Oct. 6, 2011

(65) Prior Publication Data
US 2012/0318052 A1  Dec. 20, 2012

(30) Foreign Application Priority Data
Mar. 29, 2010  (JP) .................. 2010-074735

(51) Int. Cl.
*G01N 29/00* (2006.01)
(52) U.S. Cl.
USPC ........................................ 73/64.53; 73/61.79
(58) Field of Classification Search ................ 73/61.45, 73/61.49, 61.75, 61.79, 64.53
See application file for complete search history.

(56) References Cited

U.S. PATENT DOCUMENTS

| | | | |
|---|---|---|---|
| 5,235,238 A | 8/1993 | Nomura et al. | |
| 5,747,671 A * | 5/1998 | Hirota et al. | 73/61.75 |
| 2006/0091763 A1 | 5/2006 | Yoshimine et al. | |
| 2008/0047331 A1 | 2/2008 | Wakamatsu et al. | |

FOREIGN PATENT DOCUMENTS

| | | |
|---|---|---|
| JP | 03-071038 A1 | 3/1991 |
| JP | 2006-504955 A1 | 2/2006 |
| JP | 2008-026099 A1 | 2/2008 |
| JP | 2009-031233 A1 | 2/2009 |
| WO | 2006/064951 A1 | 6/2006 |
| WO | 2007/018187 A1 | 2/2007 |

OTHER PUBLICATIONS

International Search Report for PCT/JP2010/072163 mailing date of Jan. 25, 2011.
Nagai H. et al., "Development of Multichannel Wireless-Electrodeless Quartz Crystal Microbalance", Extended Abstracts (The 56th Spring Meeting 2009), The Japan Society of Applied Physics and Related Societies No. 3, Mar. 30, 2009, pp. 1347, With partial English Translation.

* cited by examiner

*Primary Examiner* — Daniel Larkin
*Assistant Examiner* — Jamar Ray
(74) *Attorney, Agent, or Firm* — Westerman, Hattori, Daniels & Adrian, LLP

(57) ABSTRACT

A detection device (10) includes: covers (1-3); an oscillator (4); antennas (9, 11, 12), a testing space (13), and a minute space (14). The testing space (13) and minute space (14) are formed in the covers (1-3). The minute space (14) is open to the testing space (13). The oscillator (4) is disposed in the testing space (13) such that its edge portions are inserted into the minute space (14). The antenna (9) works together with the antenna (12) to apply an electromagnetic field to the oscillator (4). The antenna (11) works together with the antenna (12) to receive a reception signal composed of a vibration signal from the oscillator (4).

14 Claims, 24 Drawing Sheets

Fig.13
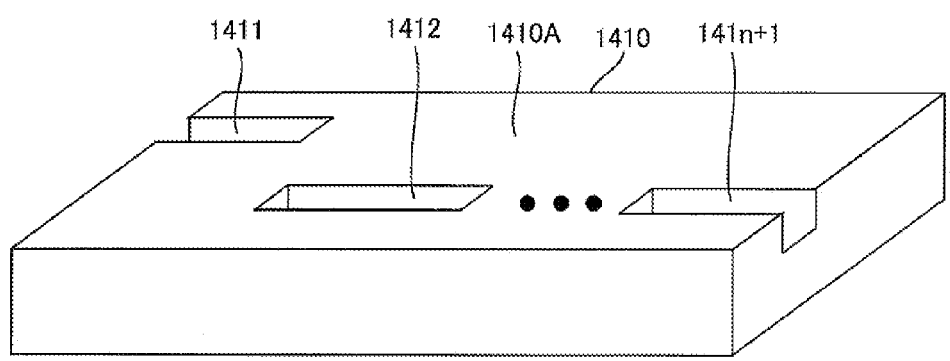
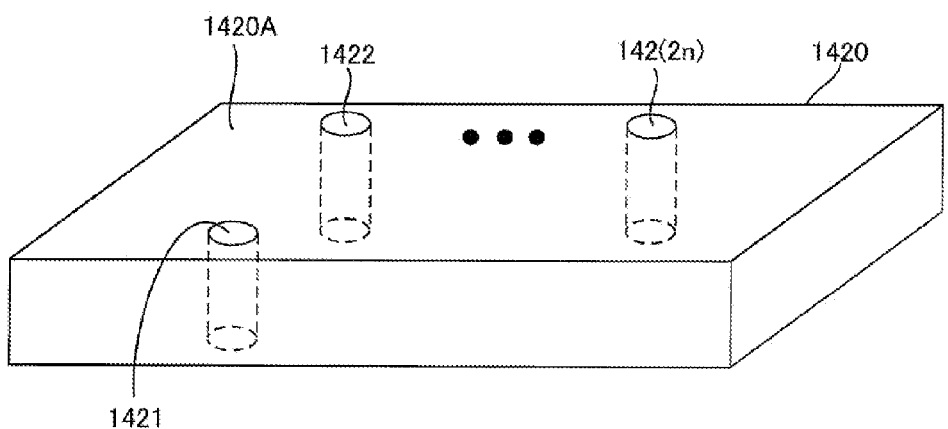

Fig.14
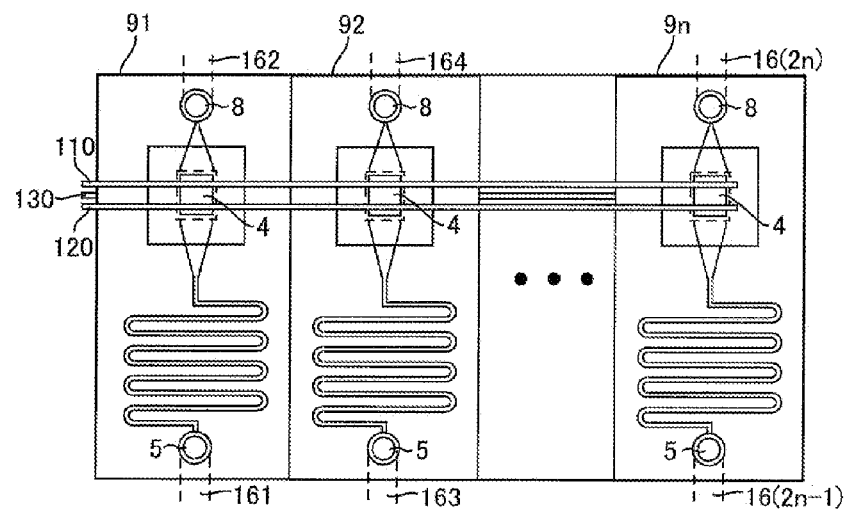
(a)
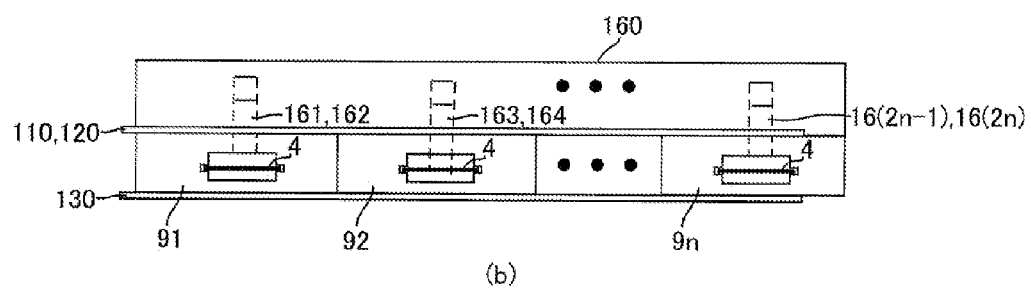
(b)

(a)　　　　　　　　(b)

DETECTION DEVICE

TECHNICAL FIELD

The present invention relates to a detection device using an oscillator.

BACKGROUND ART

A resonance oscillator-based mass detector that wirelessly detects a change in the resonance frequency of a piezoelectric oscillator without using an electrode to sense material to be detected is known (see Patent Document 1).

This resonance oscillator-based mass detector includes a piezoelectric oscillator, a sample supply means, an electric field supply means and a signal analyzer. The electric field supply means includes an input means for inputting a voltage and a receiving means that receives signals of vibrations of the piezoelectric oscillator.

When an electric field for oscillation is applied, the piezoelectric oscillator vibrates due to piezoelectric effects. The sample supply means supplies sample matter onto the surface of the piezoelectric oscillator. The input means of the electric field supply means inputs a voltage to apply an electric field for oscillation to the piezoelectric oscillator. The receiving means of the electric field supply means receives signals of vibrations of the piezoelectric oscillator. Based on the vibrations of the piezoelectric oscillator whose signals have been receive by the receiving means, the signal analyzer detects a change in the resonance frequency caused by material to he detected adhering to the piezoelectric oscillator in order to detect the material to be detected.

PRIOR ART DOCUMENTS

Patent Documents

Patent Document 1: JP2008-26099A

SUMMARY OF THE INVENTION

Problems(s) to be Solved by the Invention

However, it is difficult to ensure stable vibration of the piezoelectric oscillator in the resonance oscillator-based mass detector disclosed in Patent Document 1.

The present invention was made to solve this problem. An object of the present invention is to provide a detection device that can ensure stable vibration of the oscillator.

Means to Solve the Problems(s)

According to an embodiment of the present invention, a detection device includes: a cover; an inlet path; an outlet path; an oscillator; and a first to third antennas. The cover includes, in its interior, a testing space into which liquid to be tested is introduced, and a minute space that is open to the testing space. The inlet path is provided in the cover to introduce the liquid into the testing space. The outlet path is provided in the cover to discharge the liquid from the testing space. The oscillator is disposed in the testing space, and has a size that is larger than that of the testing space and has an edge portion inserted into the minute space. The first antenna is connected with a ground potential. The second antenna works together with the first antenna to apply an electromagnetic field to the oscillator. The third antenna works together with the first antenna to receive, from the oscillator, a reception signal composed of a vibration signal produced while the oscillator vibrates.

Preferably, the cover is composed of a first to third covers. The first cover includes, on one main surface, a first recess having a generally U-shaped cross section and a second recess continuing from an edge of the first recess and having a generally L-shaped cross section. The second cover includes a through-hole having substantially the same size as the first recess, the through-hole facing the first recess and a portion of the second cover other than the through-hole being in contact with the one main surface of the first cover to form the minute space. The third cover is disposed in contact with a side of the second cover that is opposite a side in contact with the first cover and, together with the first recess and the through-hole, forms the testing space.

Preferably, the first and third covers are made of glass, and the second cover is made of silicon.

Preferably, the cover further includes m (m is a positive integer) projection formed on a bottom surface of the minute space below the edge portion of the oscillator inserted into the minute space. The edge portion of the oscillator is disposed on the m projection.

Preferably, the m projection includes three or more projections that support the oscillator generally horizontally.

Preferably, the cover further includes k (k is an integer not smaller than 2) support members that support a portion of a side of the oscillator.

According to another embodiment of the present invention, a detection device includes: a cover; a plurality of inlet paths; a plurality of outlet paths: a plurality of oscillators: and a first to third antennas. The cover includes, in its interior, a plurality of testing spaces into which liquid to be tested is introduced, and a plurality of minute spaces provided to correspond to the plurality of testing spaces and that are open to their corresponding testing spaces. The plurality of inlet paths are provided in the cover to correspond to the plurality of testing spaces and introduce the liquid into their corresponding testing spaces. The plurality of outlet paths are provided in the cover to correspond to the plurality of testing spaces and discharge the liquid from their corresponding testing spaces. The plurality of oscillators are provided to correspond to the plurality of testing spaces, each oscillator being disposed in its respective testing space and having a size larger than that of this testing space and having an edge portion inserted into its respective minute space. The first antenna is connected with a ground potential. The second antenna works together with the first antenna to apply an electromagnetic field to the plurality of oscillators. The third antenna works together with the first antenna to receive, from the plurality of oscillators, a reception signal composed of a vibration signal produced while each oscillator vibrates.

Preferably, the detection device further includes an auxiliary cover. The auxiliary cover is disposed in contact with the cover and has a plurality of auxiliary paths. Each of the plurality of auxiliary paths connects one of the outlet paths provided to correspond to one of two adjacent testing spaces with one of the inlet paths provided to correspond to the other of the two testing spaces.

Preferably, the detection device further includes an auxiliary cover. The auxiliary cover is disposed in contact with the cover and has a plurality of auxiliary paths provided to correspond to the plurality of testing spaces. Each of the plurality of auxiliary paths is composed of a first auxiliary path that introduces the liquid from an outside into one of the inlet paths provided to correspond to its respective testing space and a second auxiliary path that discharges to the outside the liquid from one of the outlet paths provided to correspond to its respective testing space.

According to yet another embodiment of the present invention, a detection device includes: a plurality of unit elements; and a first to third antennas. The first antenna is connected with a ground potential. The second antenna works together with the first antenna to apply an electromagnetic field to a plurality of oscillators contained in the plurality of unit elements. The third antenna works together with the first antenna to receive, from the plurality of oscillators, a reception signal composed of a vibration signal produced while each oscillator vibrates. Each of the plurality of unit elements includes a cover, an inlet path, an outlet path, and an oscillator. Each cover includes, in its interior, a testing space into which liquid to be tested is introduced and a minute space open to the testing space. The inlet path is provided in the cover and introduces the liquid into the testing space. The outlet path is provided in the cover and discharges the liquid from the testing space. The oscillator is disposed in the testing space and has a size larger than that of the testing space and has an edge portion inserted into the minute space.

Preferably, the detection device further includes an auxiliary cover. The auxiliary cover is disposed in contact with the covers included in the plurality of unit elements and includes a plurality of auxiliary paths each connecting two adjacent ones of the testing spaces contained in the plurality of unit elements. Each of the plurality of auxiliary paths connects one of the outlet paths provided to correspond to one of two such testing spaces with one of the inlet paths provided to correspond to the other one of the two testing spaces.

Preferably, the detection device further includes an auxiliary cover. The auxiliary cover is disposed in contact with the covers included in the plurality of unit elements and includes a plurality of auxiliary paths provided to correspond to the testing spaces contained in the plurality of unit elements. Each of the plurality of auxiliary paths is composed of a first auxiliary path that introduces the liquid from an outside into one of the inlet paths provided to correspond to its respective testing space and a second auxiliary path that discharges the liquid to the outside from one of the outlet paths provided to correspond to its respective testing space.

Preferably, the oscillators have a generally identical thickness.

Preferably, the oscillators have different thicknesses.

Effects of the Invention

According to embodiments of the present invention, a detection device includes an oscillator having an edge portion inserted into a minute space. As a result, the oscillator vibrates freely when the second antenna works together with the first antenna to apply an electromagnetic field to the oscillator.

Thus, stable vibration of an oscillator can be ensured.

BRIEF DESCRIPTION OF THE DRAWINGS

FIG. 13 illustrates the configuration of the cover shown in FIG. 12.

FIG. 14 illustrates another specific example of the detection device shown in FIG. 11.

EMBODIMENTS FOR CARRYING OUT THE INVENTION

Embodiments of the present invention will be described in detail with reference to the drawings. The identical or corresponding parts throughout the drawings are labeled with the same characters and their description will not be repeated.

Figure 1:
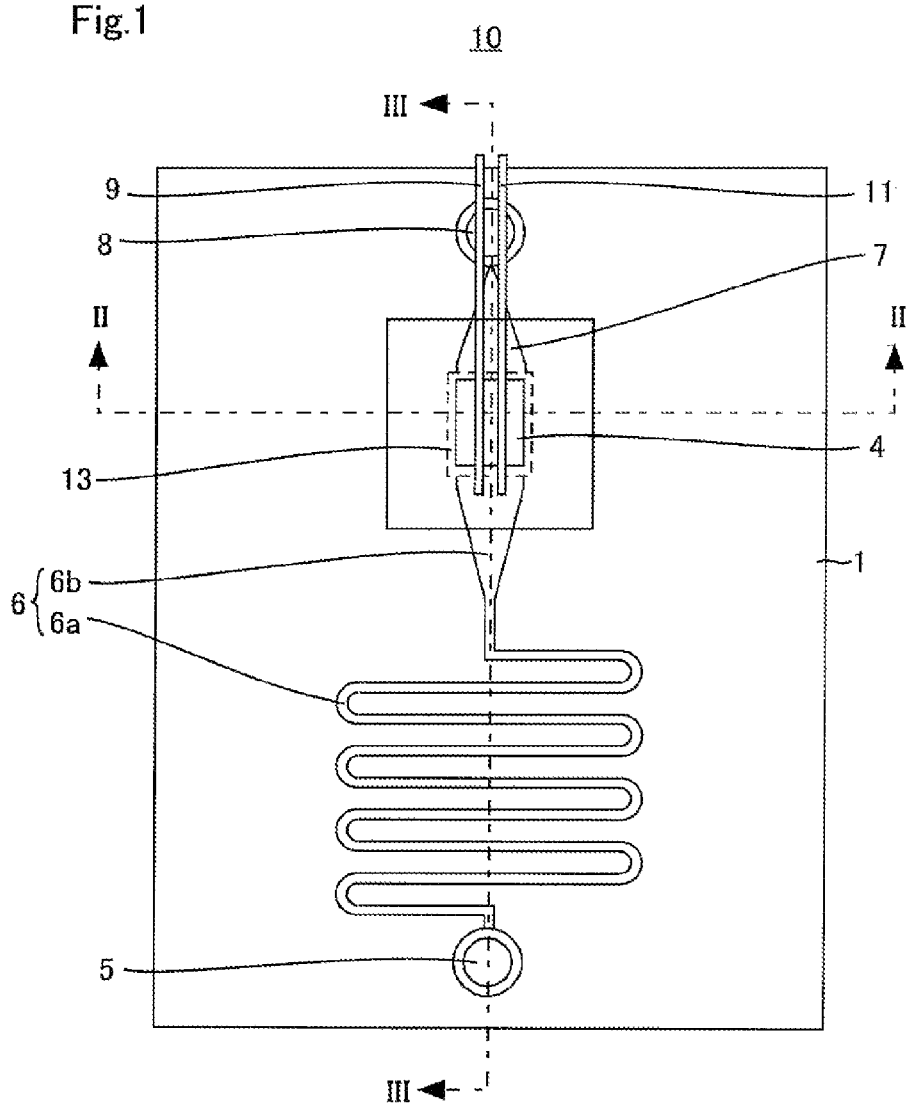
FIG. 1 is a plan view of a detection device according to an embodiment of the present invention.
Figure 2:
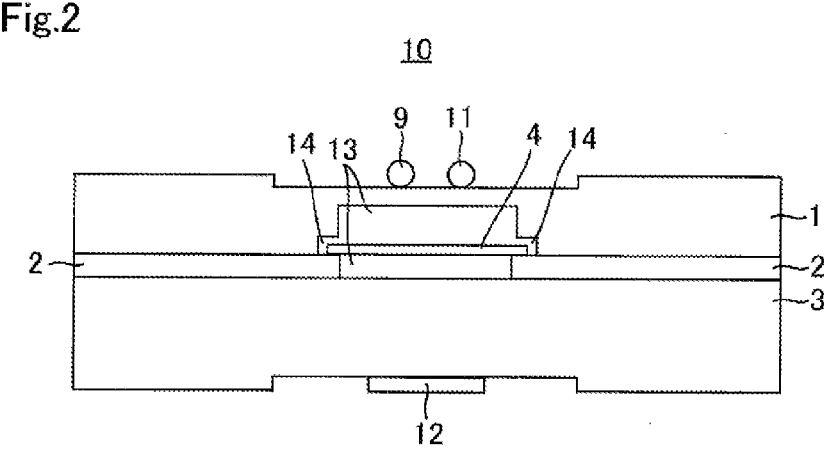
FIG. 2 is a cross-sectional view of the detection device taken on line shown in FIG. 1.
Figure 3:
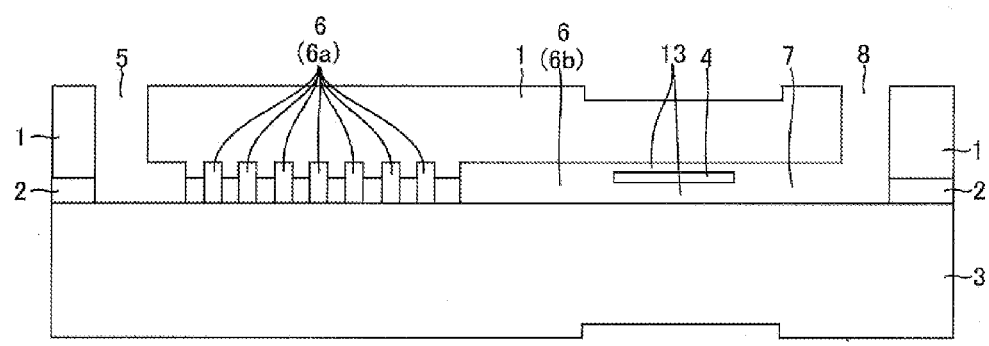
FIG. 3 is a cross-sectional view of the detection device taken on line shown in FIG. 1.

FIG. 1 is a plan view of a detection device according to an embodiment of the present invention. FIG. 2 is a cross-sectional view of the detection device taken on line II-II shown in FIG. 1. FIG. 3 is a cross-sectional view of the detection device taken on line III-III shown in FIG. 1.

Referring to FIGS. 1 to 3, the detection device 10 according to an embodiment of the present invention includes covers 1 to 3, an oscillator 4, an inlet port 5, an inlet path 6, an outlet path 7, an outlet port 8 and antennas 9, 11 and 12.

The cover 1 is made of glass, for example, and has a rectangular planar shape. The cover 1 has a thickness of 200 μm, for example.

The cover 2 is made of silicon (Si), for example, and has a rectangular planar shape. The cover 2 has a thickness of 50 μm, for example.

The cover 3 is made of glass, for example, and has a rectangular planar shape. The cover 3 has a thickness of 300 μm, for example.

The cover 2 is disposed in contact with the covers 1 and 3, and the cover 3 is disposed in contact with the cover 2. In this case, the cover 2 is joined to the cover 1 using anodic bonding, while the cover 3 is joined to the cover 2 using anodic bonding. As a result, the covers 1 to 3 form a testing space 13 and minute space 14 in its interior.

The testing space 13 is a space into which liquid to be tested is to be introduced. The minute space 14 is open to the testing space 13.

The oscillator 4 is made of crystal, for example, and has a generally rectangular planar shape. The oscillator 4 has a thickness of 10 μm, for example, and has sizes of 3 mm×3 mm, for example. The oscillator 4 is disposed in the testing space 13 and its edge portions are inserted into the minute space 14.

The inlet port 5 is provided in the covers 1 and 2. The inlet port 5 is a port through which liquid to be tested is introduced into the detection device 10 from the outside. The inlet path 6 is provided in the covers 1 and 2. The inlet path 6 has one end connected to the inlet port 5 and the other end connected to the testing space 13 and minute space 14. The inlet path 6 is composed of inlet paths 6a and 6b. The inlet path 6a winds through and has one end connected to the inlet port 5 and the other end connected to the inlet path 6b. The inlet path 6b has one end connected to the inlet path 6a and the other end connected to the testing space 13. The inlet path 6a winds through in order to stabilize the flow of liquid to be tested.

The outlet path 7 has one end connected to the testing space 13 and the other end connected to the outlet port 8. The outlet port 8 is provided in the covers 1 and 2. The outlet port 8 is a port through which liquid to be tested is discharged to the outside from the detection device 10.

Each of the antennas 9, 11 and 12 is made of a copper wire with a diameter in the range of 0.2 mm φ to 1 mm φ, for example. The antennas 9 and 11 are disposed along the top surface of the cover 1. Each of the antennas 9 and 11 has one end located above the oscillator 4 and the other end located outside the detection device 10. The antenna 12 is disposed along the bottom surface of the cover 3. The antenna 12 has one end located below the oscillator 4 and the other end located outside the detection device 10.

Thus, the antennas 9 and 11 are disposed on the same side of the device relative to the oscillator 4, while the antenna 12 is disposed on the side of the device opposite the side with the antennas 9 and 11 relative to the oscillator 4.

The oscillator 4 vibrates when an electromagnetic field is applied by the antennas 9 and 12. The inlet path 6 directs liquid introduced through the inlet port 5 to the testing space 13. The outlet path 7 directs liquid in the testing space 13 to the outlet port 8.

The antenna 9 works together with the antenna 12 to apply an electromagnetic field to the oscillator 4. The antenna 11 works together with the antenna 12 to receive a reception signal composed of a vibration signal produced while the oscillator 4 vibrates due to an applied electromagnetic field. The antenna 12 is connected to the ground potential.

Thus, the detection device 10 detects vibrations of the oscillator 4 in a contactless manner to detect material to be detected in liquid to be tested.

Figure 4:
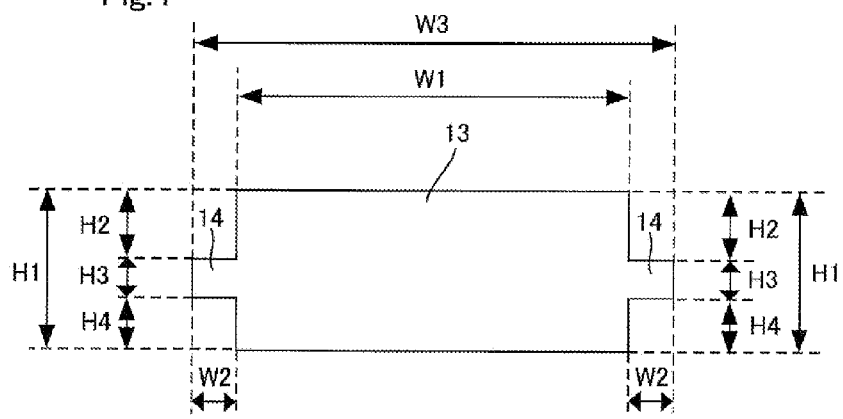
FIG. 4 is an enlarged view of the testing space and minute space shown in FIG. 2.

FIG. 4 is an enlarged view of the testing space 13 and minute space 14 shown in FIG. 2. Referring to FIG. 4, the testing space 13 has a width W1 and a height H1. The width W1 is 2.98 mm, for example. The height H1 is in the range of 120 to 130 μm, for example.

The height H1 satisfies H1=H2+H3+H4. The heights H2 and H4 are 50 μm each, for example. The height H3 is in the range of 20 to 30 μm, for example.

The minute space 14 has a width W2 and a height H3. The width W2 is 15 μm, for example.

Accordingly, the total width W3 of the testing space 13 and minute space 14 is given by W3=W1+2×W2, which means 3.01 mm.

Figure 5:
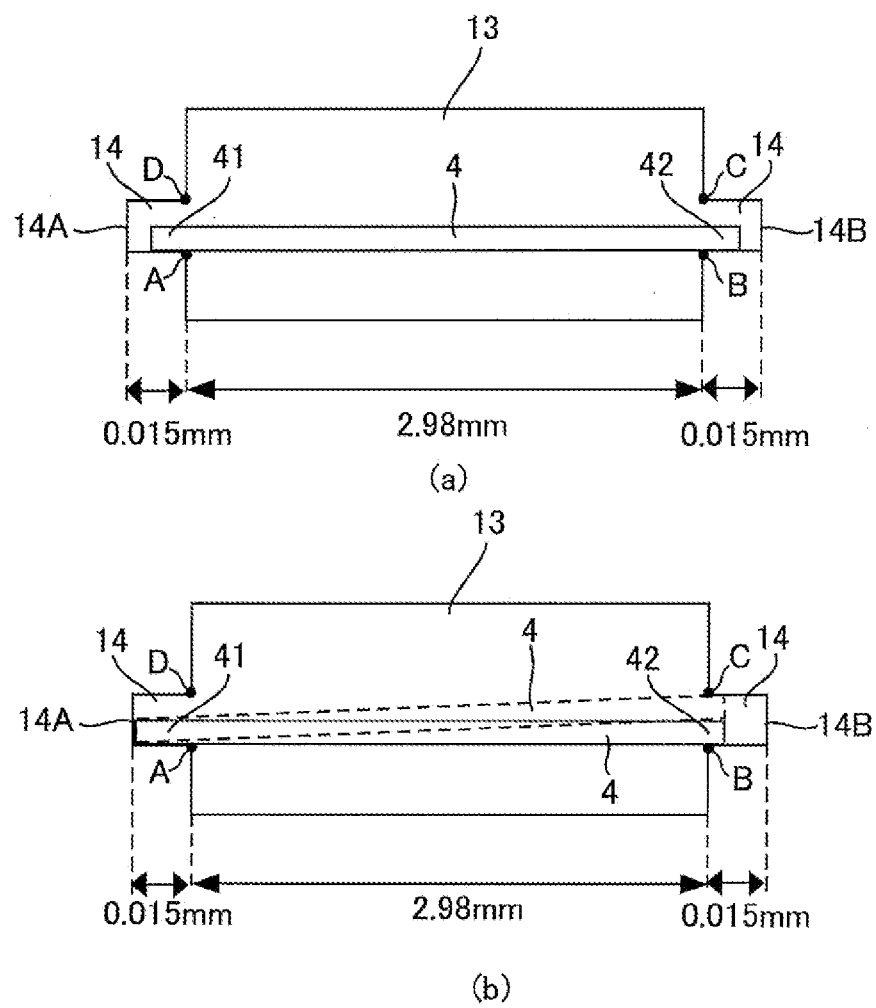
FIG. 5 illustrates the specific sizes of the testing space and minute space shown in FIG. 2.

FIG. 5 illustrates the specific sizes of the testing space 13 and minute space 14 shown in FIG. 2. As discussed above, the length of each side of the oscillator 4 is 3 mm. Accordingly, if the oscillator 4 is located in the middle of the testing space 13, one edge portion 41 of the oscillator 4 is inserted 10 μm into one minute space 14 portion, while another edge portion 42 of the oscillator 4 is inserted 10 μm into another minute space 14 portion. The distance between the edge portion 41 and the sidewall 14A of the minute space 14 is 5 μm, and the distance between the edge portion 42 and the sidewall 14B of the minute space 14 is 5 μm. The distance L1 between point A and point C is in the range from $((2.98)^2+(0.02)^2)^{1/2}$ to $((2.98)^2+(0.03)^2)^{1/2}$=2.98006 mm to 2.98015 mm. The distance L2 between point B and point D is equal to the distance L1 between point A and point C. Thus, since each of the distances L1 and L2 is smaller than the length of each side of the oscillator 4 (=3 mm), the edge portions 41 and 42 of the oscillator 4 remain inserted into the minute space 14 (see FIG. 5(a)).

When one edge of the oscillator 4 is in contact with the sidewall 14A of the minute space 14, the distance between the other edge of the oscillator 4 and the sidewall 14B of the minute space 14 is 10 μm. Even when the oscillator 4 rotates counterclockwise, the edge portions 41 and 42 of the oscillator 4 remain inserted into the minute space 14, as indicated by dotted lines. Similarly, when the oscillator 4 rotates clockwise, the edge portions 41 and 42 of the oscillator 4 remain inserted into the minute space 14 (see FIG. 5(b)).

Thus, the edge portions 41 and 42 of the oscillator 4 remain inserted into the minute space 14 even when the oscillator 4 moves within the testing space 13 and minute space 14. In other words, the oscillator 4 never moves out the minute space 14.

Figure 6:
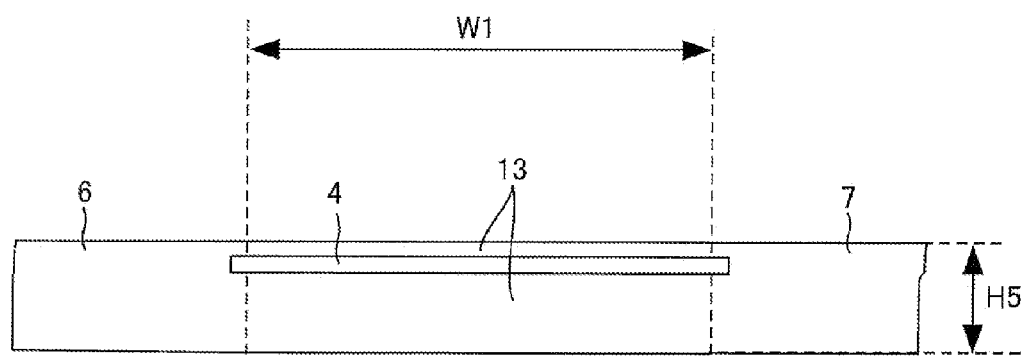
FIG. 6 is an enlarged view of the inlet path, outlet path and testing space shown in FIG. 3.

FIG. 6 is an enlarged view of the inlet path 6, outlet path 7 and testing space 13 shown in FIG. 3.

Referring to FIG. 6, the testing space 13 has the dimensions set forth above. The height H5 of the inlet path 6 and outlet path 7 is 80 μm, for example, and thus larger than the height H4 set forth above. As a result, liquid to be tested is introduced onto the both sides of the oscillator 4 from the inlet path 6.

Since the widths of the inlet path 6 and outlet path 7 (the lengths in the direction perpendicular to the plane of paper in FIG. 6) are smaller than the length of each side of the oscillator 4, the oscillator 4 never moves out the minute space 14 into the inlet path 6 or outlet path 7 when viewed along the cross section taken on line shown in FIG. 1.

Thus, the detection device 10 is configured such that the periphery of the oscillator 4 never moves out the minute space 14.

Figure 7:
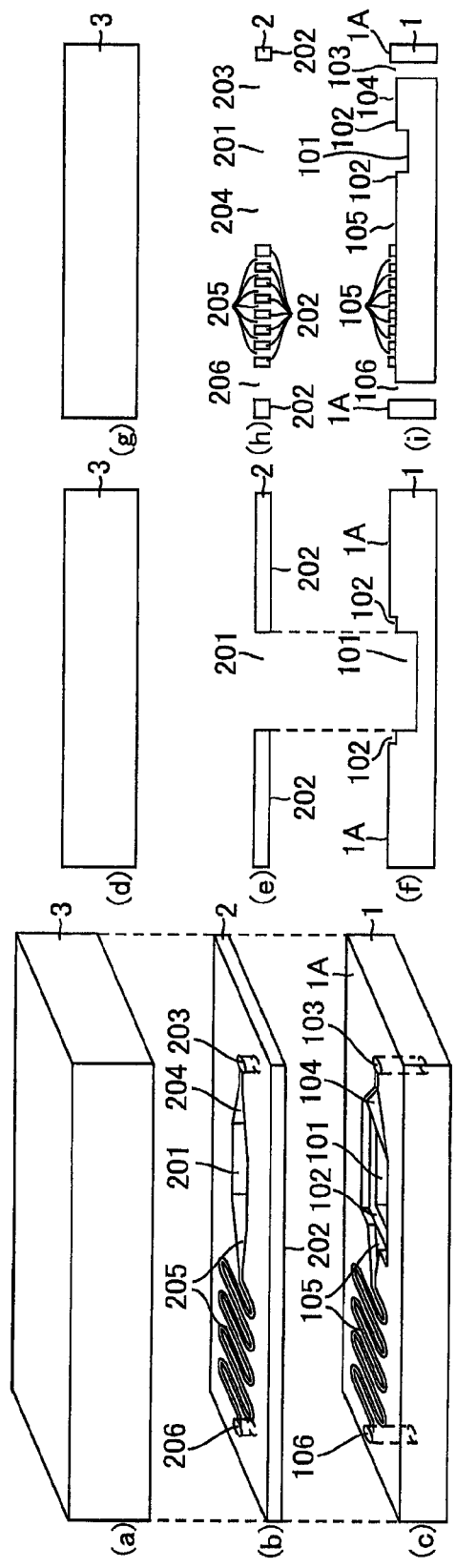
FIG. 7 is a perspective view and cross sectional views of the three covers shown in FIG. 2.

FIG. 7 is a perspective view and cross sectional views of the three covers 1 to 3 shown in FIG. 2. It should be noted that FIG. 7 shows the positional relationship between the cover 1 and cover 3 reversed in the top-to-bottom direction. The cross sections of (d) to (f) of FIG. 7 are taken on line II-II shown in FIG. 1, while the cross sections of (g) to (i) of FIG. 7 are taken on line III-III shown in FIG. 1.

Referring to FIG. 7, the cover 1 includes recesses 101, 102, 104 and 105 and through-holes 103 and 106. The recess 101 has a generally U-shaped cross section. The recess 101 has a generally rectangular planar shape. In this case, the length of each side of the rectangle is equal to the width W1 set forth above (=2.98 mm). The recess 101 has a depth equal to the height H2 set forth above (=50 μm).

The recess 102 is provided in continuation with the edges of the recess 101 and has a generally L-shaped cross section. The recess 102 has a width equal to the width W2 set forth above (=15 μm) and a depth equal to the H3 (=20 to 30 μm). The recess 102 is provided around the recess 101.

The through-hole 103 runs through the cover 1. The recess 104 is provided between the recess 102 and the through-hole 103. The recess 104 has a depth equal to the height H5 set forth above (=80 μm).

The recess 105 is provided between the recess 102 and the through-hole 106. The recess 105 has a depth equal to the height 115 set forth above (=80 μm). The through-hole 106 runs through the cover 1.

The cover 2 includes through-holes 201, 203 to 206. The through-hole 201 has the same shape and the same dimensions as the recess 101 of the cover 1.

By disposing the cover 2 such that the through-holes 201, 203 to 206 face the recess 101, through-hole 103, recesses 104 and 105 and through-hole 106, respectively, while the portions 202 of the cover other than the through-holes 201, 203 to 206 are in contact with one main surface 1A of the cover 1, the inlet port 5, the inlet path 6, the outlet path 7, the outlet port 8 and the minute space 14 are formed. Then, by disposing the cover 3 in contact with the side of the cover 2 opposite the side thereof that is in contact with the cover 1, a testing space 13 is formed.

The cover 1 is joined to the cover 2 using anodic bonding, where a voltage of 400 V is applied at a temperature of 200° C. The cover 2 is joined to the cover 3 using anodic bonding, where a voltage of 400 V is applied at a temperature of 200° C.

As discussed above, the detection device 10 is configured such that the edge portions of the oscillator 4 are inserted into the minute space 14. As a result, the oscillator 4 is not held by the covers 1 to 3, and thus vibrates freely when an electromagnetic field is applied by the antennas 9 and 12.

Thus, stable vibration of the oscillator 4 can be ensured.

Figure 8:
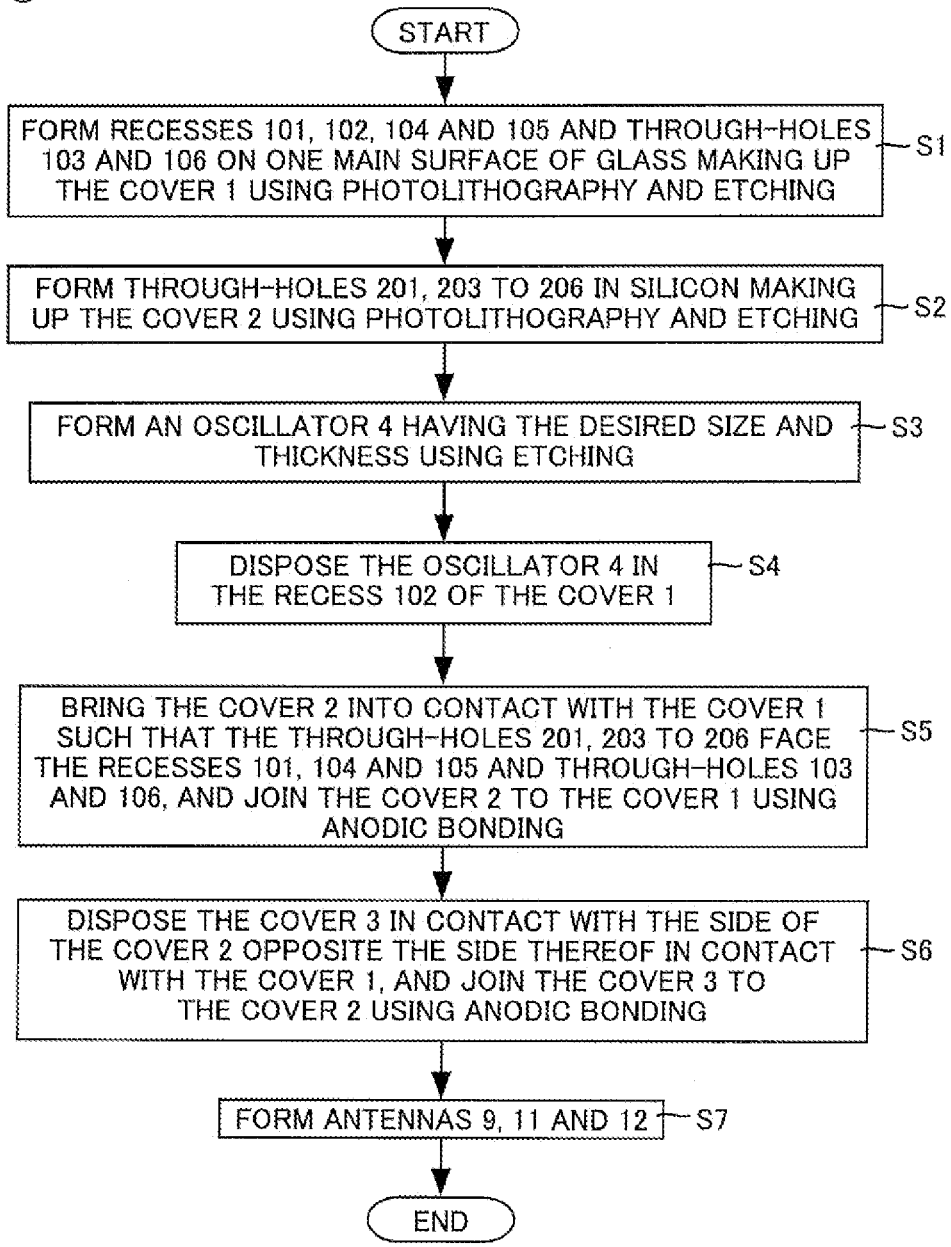
FIG. 8 is a process chart illustrating a method of manufacturing a detection device as shown in FIGS. 1 to 3.

FIG. 8 is a process chart illustrating a method of manufacturing a detection device 10 as shown in FIGS. 1 to 3. Referring to FIG. 8, after manufacture of a detection device 10 is initiated, recesses 101, 102, 104 and 105 and through-holes 103 and 106 are formed on one main surface of glass making up the cover 1 using photolithography and etching in semiconductor technology (step S1). In this case, since the recesses 101, 102, 104 and 105 and through-holes 103 and 106 have different depths, and thus application of resist and patterning and etching of resist are repeated to make shallower structures before deeper ones. As a result, the recesses 101, 102, 104 and 105 and through-holes 103 and 106 are formed. In embodiments of the present invention, etching includes dry etching and wet etching (the same shall apply hereinafter).

Thereafter, using photolithography and etching through-holes 201, 203 to 206 are formed in silicon making up the cover 2 (step S2).

Then, an oscillator 4 having the desired size and thickness is formed using etching and mechanical polishing (step S3).

Subsequently, the oscillator 4 is disposed relative to the cover 1 such that its edge portions are located above the recess 102 of the cover 1 (step S4).

Then, the cover 2 is contacted with the cover 1 such that the through-holes 201, 203 to 206 face the recesses 101, 104 and 105 and through-holes 103 and 106, and then the cover 2 is joined to the cover 1 using anodic bonding, as discussed above (step S5). Thus, an inlet port 5, inlet path 6, outlet path 7 and outlet port 8 and a minute space 14 are formed.

Thereafter, the cover 3 is disposed in contact with the side of the cover 2 opposite the side thereof that is in contact with the cover 1, and then the cover 3 is joined to the cover 2 using anodic bonding, as discussed above (step S6). Thus, a testing space 13 is formed.

Then, antennas 9, 11 and 12 are formed (step S7). This results in a completed detection device 10.

Figure 9:
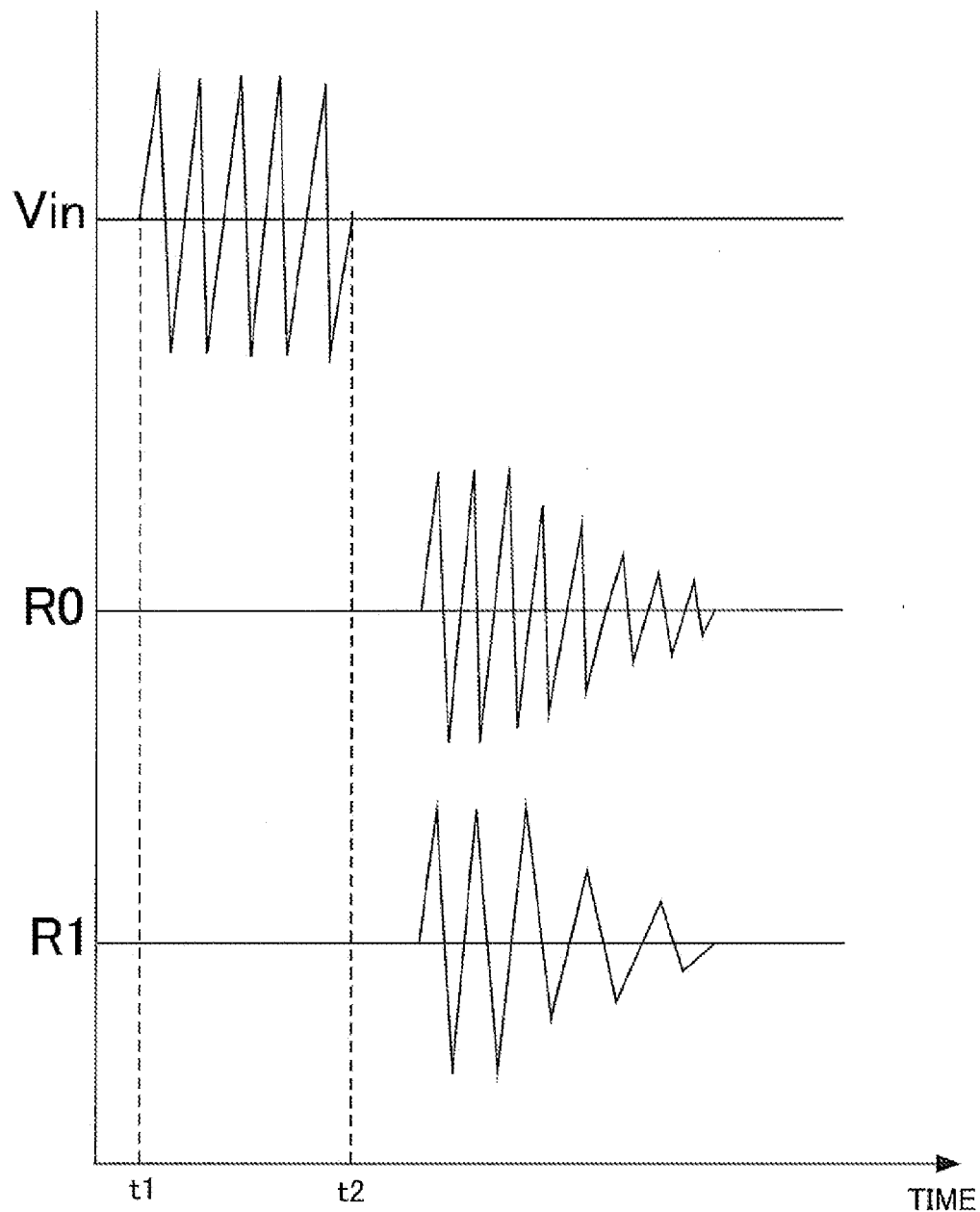
FIG. 9 is a timing chart for the input voltage Vin and reception signals R.
Figure 10:
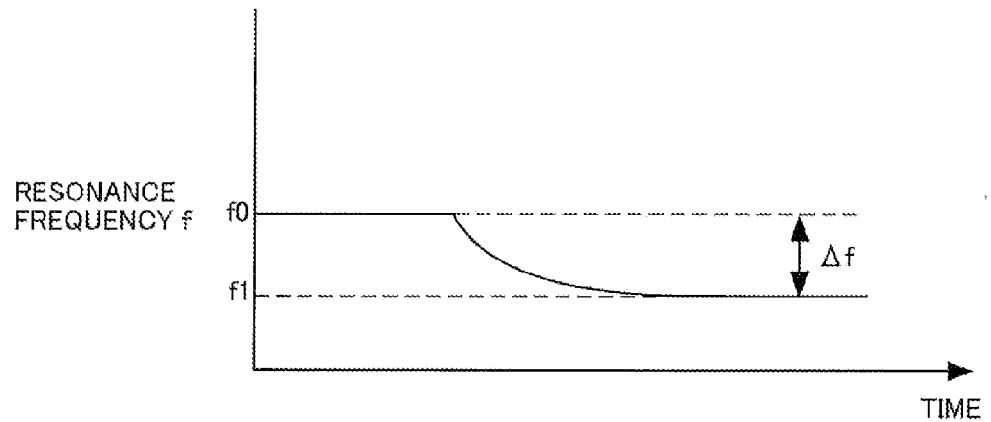
FIG. 10 is a timing chart for resonance frequency.

FIG. 9 is a timing chart for the input voltage Vin and reception signals R. FIG. 10 is a timing chart for resonance frequency.

Referring to FIGS. 9 and 10, a method of detecting material to be detected using the detection device 10 will be described. When material to be detected is to be detected, an application circuit (not shown) applies to the antenna 9 an input, voltage Vin composed of a vibration waveform from time t1 to time t2. Then, at time t2, the application circuit stops applying the input voltage Vin to the antenna 9.

As such, if the distance between the antenna 9 and antenna 12 is represented by L, the antenna 9 works together with the antenna 12 to apply to the oscillator 4 an electric field for oscillation E represented by Vin/L (=Vin/L) between time t1 and time t2.

When the electric field for oscillation E (=Vin/L) is applied, the oscillator 4 resonates due to inverse piezoelectric effects to generate a distribution of potentials on its surface.

Then, the antenna 11 works together with the antenna 12 to receive the distribution of potentials generated on the surface of the oscillator 4 as a reception signal R composed of a vibration waveform. In this case, if no material to be detected is adherent to the oscillator 4, the antenna 11 receives a reception signal R0 composed of a vibration waveform and, if material to be detected is adherent to the oscillator 4, receives a reception signal R1 composed of a vibration waveform. Then, the antenna 11 outputs the received reception signal R0 or R1 to a detection circuit (not shown).

When the detection circuit receives the reception signal R0 from the antenna 11, it detects the resonance frequency f0 of the received reception signal R0. When the detection circuit receives the reception signal R1 from the antenna 11, it detects the resonance frequency f1 (<f0) of the received reception signal R1. The detection circuit then detects the amount of change in resonance frequency Δf=f0·f1 to sense material to be detected adhering to the oscillator 4.

When material to be detected adheres to the oscillator 4, the mass of the oscillator 4 increases such that the resonance frequency f1 of the oscillator 4 is smaller than that in the case when no material to be detected is adherent to the oscillator 4.

As such, after the input voltage Vin is applied to the antenna 9, the detection circuit receives a reception signal R from the antenna 11 and, when no material to be detected is adherent to the oscillator 4, detects the resonance frequency f0 from the reception signal R and, when material to be detected adheres to the oscillator 4, detects a resonance frequency f that gradually changes to the resonance frequency f1 (see FIG. 10). Then, the detection circuit detects the amount of change $\Delta f = f0 \cdot f1$ for the resonance frequency f to detect that material to be detected adheres to the oscillator 4.

If the resonance frequency of the oscillator 4 is represented by f, the mass of the oscillator 4 is represented by in and the amount of change in the mass of the oscillator 4 (=mass of the material to be detected) is represented by $\Delta m$, then the amount of change $\Delta f$ in the resonance frequency of the oscillator 4 is given by the following equation:

$$\Delta f = f \cdot \Delta m / m \qquad (1)$$

Thus, the amount of change $\Delta f$ in resonance frequency is proportional to the amount of change $\Delta m$ in the mass of the oscillator 4, i.e. the mass of the material to be detected, and is inversely proportional to the mass in of the oscillator 4. Accordingly, as the mass of the material to be detected increases, or the mass (=thickness) of the oscillator 4 decreases, the amount of change $\Delta f$ in the resonance frequency f increases, thereby making it easier to sense material to be detected adhering to the oscillator 4.

The detection device 10 detects material to be detected in the manner discussed above as liquid to be tested is introduced into the testing space 13 through the inlet port 5 and inlet path 6 and liquid to be tested is discharged from the testing space 13 through the outlet path 7 and outlet port 8, i.e. liquid to be tested is circulated.

In this case, since the oscillator 4 is not pinched by the covers 1 to 3, as discussed above, it vibrates freely when an electromagnetic field is applied by the antennas 9 and 12. Accordingly, stable vibration of the oscillator 4 can be ensured to enable detecting material to be detected.

When detection of material to be detected is finished, the strong acid is obtained by mixing concentrated sulfuric acid with hydrogen peroxide, where the ratio of concentrated sulfuric acid to hydrogen peroxide is 7 to 3. Then, the oscillator 4 is washed by circulating a strong acid through the inlet port 5, inlet path 6, testing space 13, minute space 14, outlet path 7, and outlet port 8.

It is noted that as the oscillator 4 is washed with a strong acid, the surface of crystal that makes up the oscillator 4 is covered with an OH group, making it easier for protein to be absorbed by the oscillator 4. In this case, protein can be easily absorbed by the oscillator 4 even if no silane coupling agent and self-assembled monolayer (SAM) agent are used.

Thereafter, ultrapure water is circulated through the inlet port 5, inlet path 6, testing space 13, minute space 14, outlet path 7 and outlet port 8 to wash the oscillator 4.

After the oscillator 4 is washed, receptor (i.e. protein) is flown through the inlet port 5; inlet path 6, testing space 13, minute space 19, outlet path 7 and outlet port 8 to allow receptor (i.e. protein) to be absorbed by the oscillator 4. Thereafter, material to be detected is detected in the manner described above.

Then, the operations set forth above are repeated to detect material to be detected.

As such, once the detection device 10 is fabricated, the detection device 10 may be used semipermanently.

Figure 11:
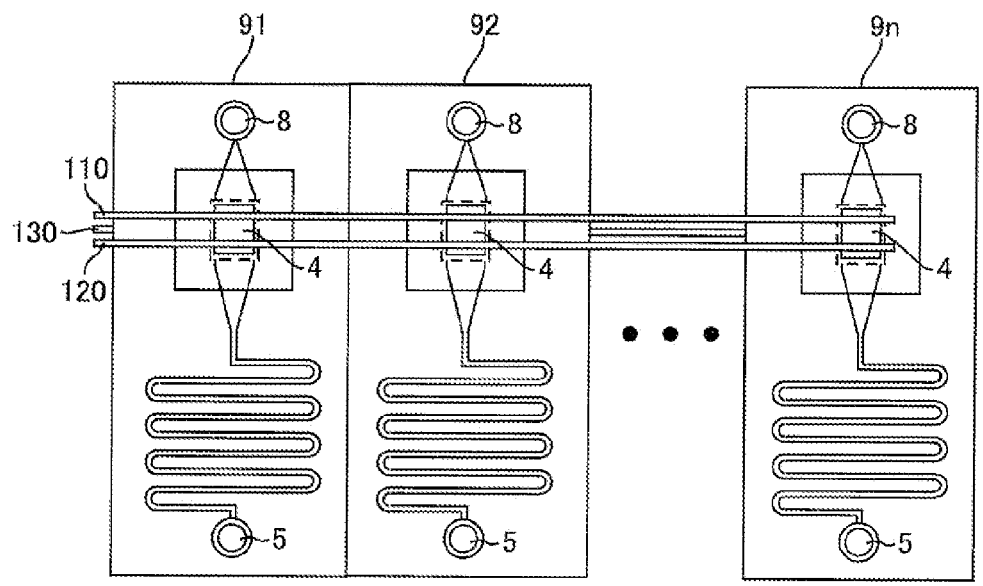
FIG. 11 is a schematic view of another detection device according to an embodiment of the present invention.

FIG. 11 is a schematic view of another detection device according to an embodiment of the present invention. The detection device according to an embodiment of the present invention may be the detection device 100 shown in FIG. 11.

Referring to FIG. 11, the detection device 100 includes unit elements 91 to 9n (n is an integer not smaller than 2) and antennas 110, 120 and 130.

Each of the unit elements 91 to 9n includes covers 1 to 3, oscillator 4, inlet port 5, inlet path 6, outlet path 7, outlet port 8, testing space 13 and minute space 14 as in the detection device 10 described above. The unit elements 91 to 9n are arranged in a row such that the direct lines that each connect an inlet port 5 with an outlet port 8 are parallel to each other, for example.

The antennas 110, 120 and 130 correspond to the antennas 9, 11 and 12 of the detection device 10, respectively. The antennas 110 and 120 are disposed on one side of the unit elements 91 to 9n above the n oscillators 4 contained in the unit elements 91 to 9n. The antenna 130 is disposed on the other side of the unit elements 91 to 9n below the n oscillators 4 contained in the unit elements 91 to 9n.

Thus, in the detection device 100, the antennas 110, 120 and 130 are shared by the n unit elements 91 to 9n.

The antenna 110 works together with the antenna 130 to apply an electromagnetic field to the n oscillators 4 of the unit elements 91 to 9n. The antenna 120 works together with the antenna 130 to receive a reception signal composed of a vibration signal produced while the n oscillators 4 of the unit elements 91 to 9n vibrate.

In the detection device 100, the n oscillators 4 of the unit elements 91 to 9n may have the same thickness or different thicknesses.

If the n oscillators 4 of the unit elements 91 to 9n have the same thickness, the detection device 100 detects the same type of material to be detected using the unit elements 91 to 9n.

On the other hand, if the n oscillators 4 of the unit elements 91 to 9n have different thicknesses, the detection device 100 detects different types of material to be detected using the unit elements 91 to 9n.

Figure 12:
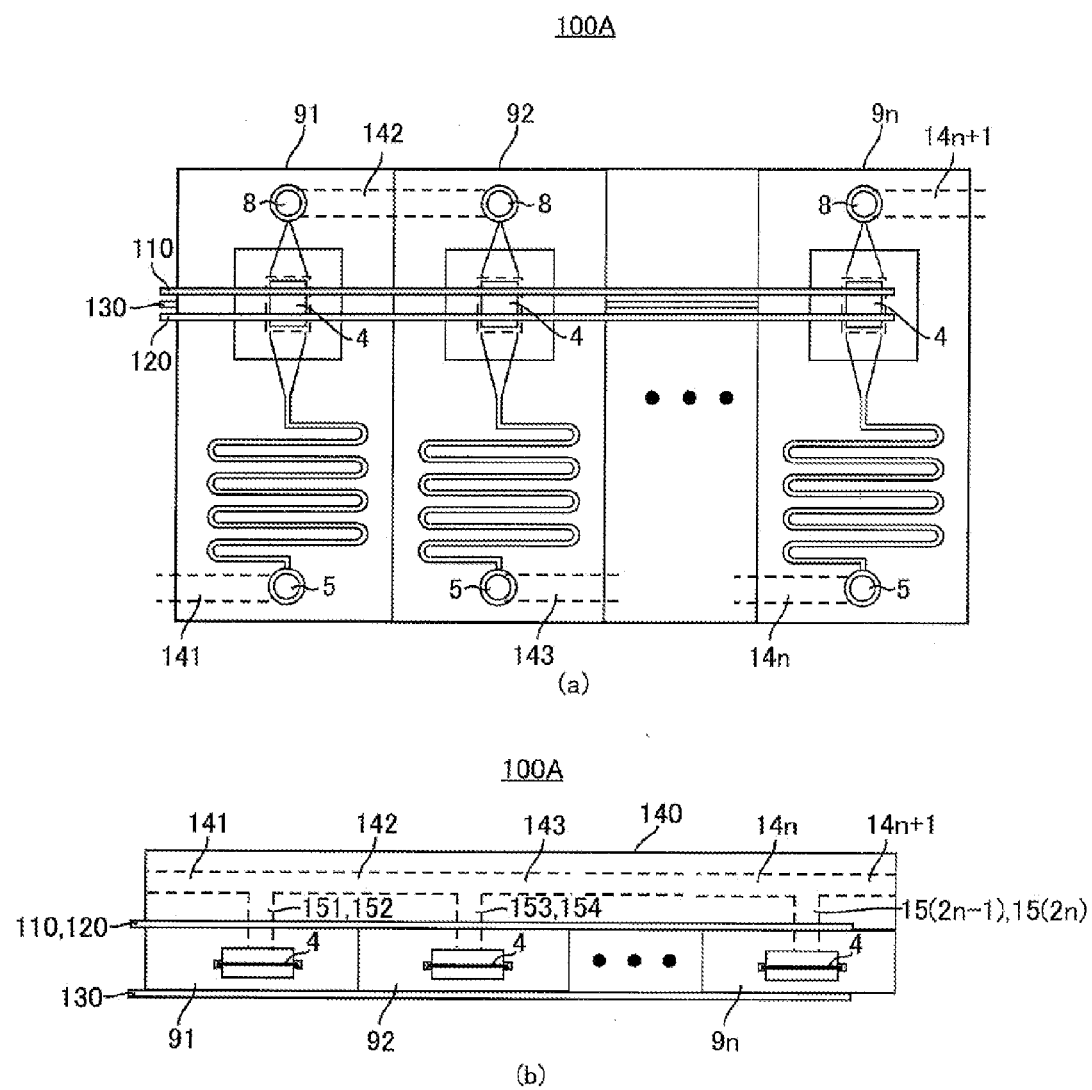
FIG. 12 illustrates a specific example of the detection device shown in FIG. 11.

FIG. 12 illustrates a specific example of the detection device 100 shown in FIG. 11. (a) of FIG. 12 shows a plan view, while (b) of FIG. 12 shows a side view.

Referring to FIG. 12, the detection device 100A is a detection device 100 plus a cover 140. The cover 140 is disposed on the unit elements 91 to 9n. The cover 140 includes auxiliary paths 141 to 14n+1 and holes 151 to 15(2n). The cover 140 is made of glass, for example.

The auxiliary path 141 has one end located on an end face of the cover 140 and the other end connected to the hole 151. The auxiliary path 142 has one end connected to the hole 152 and the other end connected to the hole 153. The auxiliary path 143 has one end connected to the hole 154. Likewise the auxiliary path 14n has the other end connected to the hole 15(2n−1) and the auxiliary path 14n+1 has one end connected to the hole 15(2n).

The hole 151 is connected to the inlet port 5 of the unit element 91. The hole 152 is connected to the outlet port 8 of the unit element 91. The hole 153 is connected to the outlet port 8 of the unit element 92. The hole 154 is connected to the inlet port 5 of the unit element 92. Likewise, the hole 15(2n−1) is connected to the inlet port 5 of the unit element 9n and the hole 15(2n) is connected to the outlet port 8 of the unit element 9n.

Liquid to be tested is introduced into the detection device 100A through the auxiliary path 141 and flows through the unit elements 91, 92, . . . , and 9n in the stated order, and is discharged to the outside through the auxiliary path 14n+1. In this case, liquid is introduced into the unit element 92 through the outlet port 8 and discharged through the inlet port 5.

Thus, the cover 140 connects the n unit elements 91 to 9n in series.

In the detection device 100A, the n oscillators 4 contained in the n unit elements 91 to 9n have the same thickness.

FIG. 13 illustrates the configuration of the cover 140 shown in FIG. 12. Referring to FIG. 13, the cover 140 includes covers 1410 and 1420. The covers 1410 and 1420 are made of glass.

The cover 1410 includes grooves 1411 to 141n+1 on one main surface 1410A. The groove 1411 has one end located on an end face of the cover 1410. The groove 141n+1 has the other end located on another end face of the cover 1410.

The cover 1420 includes through-holes 1421 to 14(2n). Each of the through-holes 1421 to 14(2n) has a diameter generally equal to the width of the grooves 1411 to 141n+1.

The cover 1410 is joined to the cover 1420 using anodic bonding as set forth above such that one main surface 1410A of the cover 1410 is in contact with one main surface 1420A of the cover 1420.

As a result, the through-hole 1421 is connected to the other end of the groove 1411, the through-hole 1422 is connected to the one end of the groove 1412, and the through-hole 142(2n) is connected to the one end of the groove 141n+1. The grooves 1411 to 141n+1 form the auxiliary paths 141 to 14n+1, respectively, as their openings on the one main surface 1410A of the cover 1410 are closed up by the one main surface 1420A of the cover 1420. The through-holes 1421 to 14(2n) form holes 151 to 15(2n), respectively.

The detection device 100A is fabricated by the following method. First, steps S1 to S5 shown in FIG. 8 are repeated n times to fabricate n unit elements 91 to 9n.

Then, the n unit elements 91 to 9n are arranged in one row as shown in FIG. 11, and antennas 110, 120 and 130 are disposed to fabricate a detection device 100.

Thereafter, grooves 1411 to 141n+1 are formed on one main surface 1410A using photolithography and etching to fabricate a cover 1410. Through-holes 1421 to 14(2n) are formed using photolithography and etching to prepare a cover 1420.

Then, the cover 1410 is joined to the cover 1420 using anodic bonding such that the one main surface 1410A of the cover 1410 is in contact with the one main surface 1420A of the cover 1420. Thus, the cover 140 is fabricated.

The cover 140 is then disposed on the n unit elements 91 to 9n such that the holes 151 to 15(2n) of the cover 140 are connected to their respective inlet ports 5 or outlet ports 8.

This results in a completed detection device 100A.

A method of detecting material to be detected with the detection device 100A will be described. Liquid to be tested is introduced into the detection device 100A through the auxiliary path 141 and liquid is discharged through the auxiliary path 14n+1 to circulate liquid through the n unit elements 91 to 9n in series.

Then, the antennas 110 and 130 apply an electromagnetic field to the n oscillators 4 of the n unit elements 91 to 9n. Thereafter, the antennas 120 and 130 receive a reception signal composed of a vibration signal from each of the n oscillators 4. Then, the amount of change $\Delta f$ in the resonance frequency of a vibration signal is detected to detect material to be detected.

When detection of material to be detected is finished, a strong acid, as discussed above, is flown through the n testing spaces 13 of the n unit elements 91 to 9n, similar to liquid to be tested, to wash the n oscillators 4.

Then, similar to liquid to be tested, ultrapure water is flown through the n testing spaces 13 of the n unit elements 91 to 9n to wash the n oscillators 4.

Thereafter, similar to liquid to be tested, receptor (i.e. protein) is flown through the n testing spaces 13 of the n unit elements 91 to 9n to allow receptor (i.e. protein) to be absorbed by the n oscillators 4. Then, material to be detected is detected in the manner described above.

Then, the operations set forth above are repeated to detect material to be detected, using the detection device 100A semipermanently.

FIG. 14 illustrates another specific example of the detection device 100 shown in FIG. 11. (a) of FIG. 14 shows a plan view, while (b) of FIG. 14 shows a side view.

Referring to FIG. 14, the detection device 100E is a detection device 100 plus a cover 160. The cover 160 is disposed on the unit elements 91 to 9n. The cover 160 includes auxiliary paths 161 to 16(2n). The cover 160 is made of glass, for example.

The auxiliary path 161 has one end located on an end face of the cover 160 and the other end connected to the inlet port 5 of the unit element 91. The auxiliary path 162 has one end connected to the outlet port 8 of the unit element 91 and the other end located on another end face of the cover 160.

The auxiliary path 163 has one end located on an end face of the cover 160 and the other end connected to the inlet port 5 of the unit element 92. The auxiliary path 164 has one end connected to the outlet port 8 of the unit element 92 and the other end located on another end face of the cover 160.

Similarly, the auxiliary path 16(2n–1) has one end located on the end face of the cover 160 and the other end connected to the inlet port 5 of the unit element 9n. The auxiliary path 16(2n) has one end connected to the outlet port 8 of the unit element 9n and the other end located on the another end face of the cover 160.

In the detection device 100B, liquid to be tested is introduced into the unit elements 91 to 9n through the auxiliary paths 161, 163, . . . , and 16(2n–1) and discharged to the outside through the auxiliary paths 162, 164, . . . , and 16(2n).

Thus, in the detection device 100B, liquid to be tested is flown into the unit elements 91 to 9n through the cover 160 in parallel.

In the detection device 100B, the n oscillators 4 contained in the n unit elements 91 to 9n may have the same thickness or different thicknesses.

Figure 15:
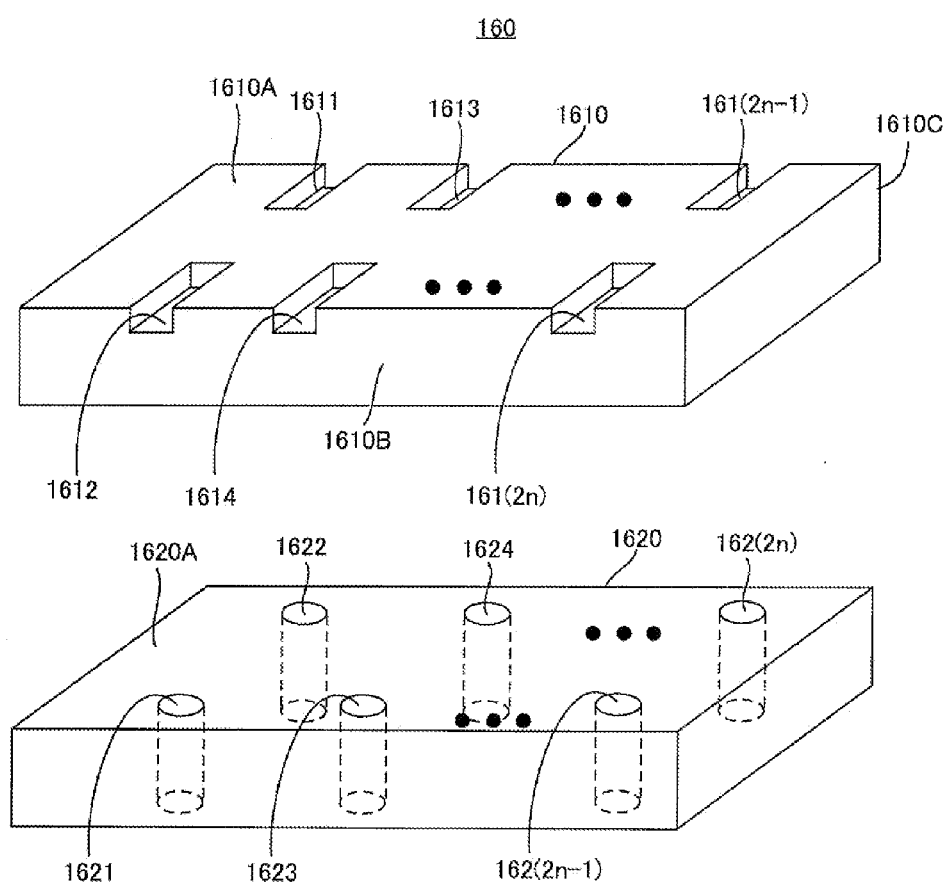
FIG. 15 illustrates the configuration of the cover shown in FIG. 14.

FIG. 15 illustrates the configuration of the cover 160 shown in FIG. 14. Referring to FIG. 15, the cover 160 is made up of covers 1610 and 1620. The covers 1610 and 1620 are made of glass.

The cover 1610 includes grooves 1611 to 161(2n) on one main surface 1610A. The groove 1611 has one end located on an end face 1610B of the cover 1610. The groove 1612 has one end located on an end face 1610C of the cover 1610.

The groove 1613 has one end located on the end face 1610B of the cover 1610. The groove 1614 has one end located on the end face 1610C of the cover 1610.

Similarly, the groove 161(2n–1) has one end located on the end face 1610B of the cover 1610, and the groove 161(2n) has one end located on the end face 1610C of the cover 1610.

The cover 1620 includes through-holes 1621 to 16(2n). Each of the through-holes 1621 to 16(2n) has a diameter generally equal to the width of the grooves 1611 to 161(2n).

The cover 1610 is joined to the cover 1620 using anodic bonding as set forth above such that the one main surface 1610A of the cover 1610 is in contact with the one main surface 1620A of the cover 1620.

As a result, the through-hole 1621 is connected to the other end of the groove 1611, the through-hole 1622 is connected to the other end of the groove 1612, the through-hole 1623 is connected to the other end of the groove 1613, the through-hole 1624 is connected to the other end of the groove 1614, and similarly, the through-hole 162(2n) is connected to the other end of the groove 161(2n–1) and the through-hole 162

(2n) is connected to the groove 161(2n). The grooves 1611 to 161(2n) and through-holes 1621 to 16(2n) form auxiliary paths 161 to 16(2n), respectively, as the openings on the one main surface 1610A of the grooves 1611 to 161(2n) are closed up by the one main surface 1620A of the cover 1620.

The detection device 100B is fabricated by the following method. First, steps S1 to S5 shown in FIG. 8 are repeated n times to fabricate n unit elements 91 to 9n.

Then, the n unit elements 91 to 9n are arranged in one row as shown in FIG. 11, and antennas 110, 120 and 130 are disposed to prepare a detection device 100.

Thereafter, grooves 1611 to 161(2n) are formed on one main surface 1610A using photolithography and etching to prepare a cover 1610. Through-holes 1621 to 16(2n) are formed using photolithography and etching to prepare a cover 1620.

Then, the cover 1610 is joined to the cover 1620 using anodic bonding such that the one main surface 1610A of the cover 1610 is in contact with the one main surface 1620A of the cover 1620. Thus, a cover 160 is prepared.

The cover 160 is then disposed on the n unit elements 91 to 9n such that the auxiliary paths 161 and 162; 163 and 164; . . . ; 16(2n−1) and 16(2n) of the cover 160 are connected to their respective inlet ports 5 or outlet ports 8.

This results in a completed detection device 100B.

A method of detecting material to be detected with the detection device 100B will be described. If the n oscillators 4 contained in the n unit elements 91 to 9n have the same thickness, liquid of the same type to be tested is introduced into the detection device 100E through the auxiliary paths 161, 163, . . . , 16(2n−1) in parallel and liquid is discharged from the auxiliary paths 162, 164, . . . , 16(2n) in parallel to circulate liquid through the n unit elements 91 and 9n in parallel.

Then, the antennas 110 and 130 apply an electromagnetic field to the n oscillators 4 of the n unit elements 91 to 9n. Thereafter, the antennas 120 and 130 receive a reception signal composed of a vibration signal from each of the n oscillators 4. Then, the amount of change $\Delta f$ resonance frequency of a vibration signal is detected to detect material to be detected.

When detection of material to be detected is finished, a strong acid, as discussed above, is flown through the n testing spaces 13 of the n unit elements 91 to 9n in parallel, similar to liquid to he tested, to wash the n oscillators 4.

Then, similar to liquid to be tested, ultrapure water is flown through the n testing spaces 13 of the n unit elements 91 to 9n in parallel to wash the n oscillators 4.

Thereafter, similar to liquid to be tested, receptor (i.e. protein) is flown through the n testing spaces 13 of the n unit elements 91 to 9n in parallel to allow receptor (i.e. protein) to be absorbed by the n oscillators 4. Then, material to be detected is detected in the manner described above.

Then, the operations set forth above are repeated to detect material to be detected, using the detection device 100B semi-permanently.

On the other hand, if the n oscillators 4 contained in the n unit elements 91 to 9n have different thicknesses, n different types of liquid are introduced into the detection device 100B through the auxiliary paths 161, 163 . . . , 16(2n) in parallel and liquid is discharged from the auxiliary paths 162, 164, . . . , 16(2n) in parallel to circulate the n types of liquid through the n unit elements 91 and 9n in parallel.

Then, the antennas 110 and 130 apply an electromagnetic field to the n oscillators 4 of the n unit elements 91 to 9n. Thereafter, the antennas 120 and 130 receive a reception signal composed of a vibration signal from each of the n oscillators 4. Then, the amount of change of in the resonance frequency of a vibration signal is detected to detect material to be detected. In this case, since the n oscillators 4 have different thicknesses, there are n different resonance frequencies of reception signals (i.e. vibration signals) received from the n oscillators 4. Thus, material to be detected in n types of liquid can be detected.

When detection of material to be detected is finished, a strong acid, as discussed above, is flown through the n testing spaces 13 of the n unit elements 91 to 9n in parallel, similar to liquid to be tested, to wash the n oscillators 4.

Then, similar to liquid to be tested, ultrapure water is flown through the n testing spaces 13 of the n unit elements 91 to 9n in parallel to wash the n oscillators 4.

Thereafter, similar to liquid to be tested, receptor (i.e. protein) is flown through the n testing spaces 13 of the n unit elements 91 to 9n in parallel to allow receptor (i.e. protein) to be absorbed by the n oscillators 4. Then, material to be detected is detected in the manner described above.

Then, the operations set forth above are repeated to detect material to be detected, using the detection device 100B semi-permanently.

In the detection device 100B, liquid may only be circulated through some of the n unit elements 91 to 9n to detect material to be detected.

Thus, in the detection device 100B, the oscillators 4 may have the same thickness or different thicknesses to detect material to be detected in the same type of liquid or n types of liquid.

Figure 16:
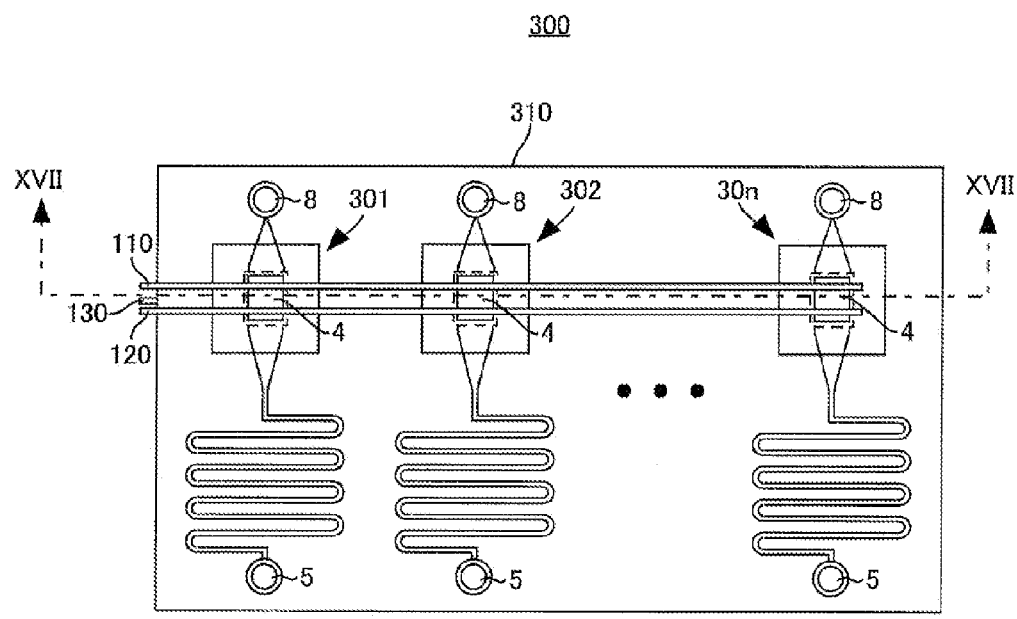
FIG. 16 is a plan view of still another detection device according to an embodiment of the present invention.
Figure 17:
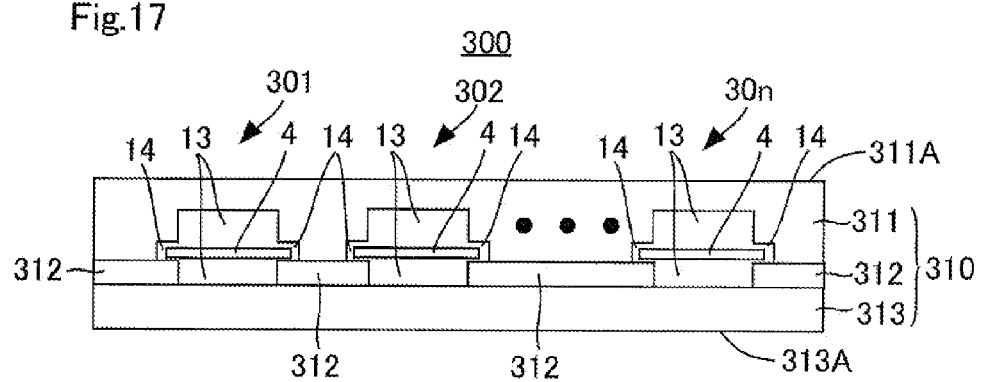
FIG. 17 is a cross-sectional view of the detection device taken on line XVII-XVII shown in FIG. 1G.

FIG. 16 is a plan view of yet another detection device according to an embodiment of the present invention. FIG. 17 is a cross-sectional view of the detection device 300 taken on line XVII-XVII shown in FIG. 16.

The detection device according to an embodiment of the present invention may be the detection device 300 shown in FIGS. 16 and 17.

Referring to FIGS. 16 and 17, the detection device 300 includes a cover 310, elements 301 to 30n and antennas 110, 120 and 130.

The cover 310 is composed of covers 311 to 313. The covers 311 and 313 are made of glass, for example. The cover 312 is made of Si, for example. The covers 311 to 313 have the same thicknesses as the covers 1 to 3, respectively, described above.

Each of the elements 301 to 30n includes the oscillator 4, the inlet port 5, the inlet path 6, the outlet path 7, the outlet port 8, the testing space 13 and the minute space 14, as set forth above. The n elements 301 to 30n are fabricated in a row in the cover 310 such that the direct lines that each connect the inlet port 5 with the outlet port 8 are parallel to each other.

The antennas 110 and 120 are disposed on the top surface 311A of the cover 311 above the n oscillators 4 contained in the n elements 301 to 30n.

The antenna 130 is disposed on the bottom surface 313A of the cover 313 below the n oscillators 4 contained in the n elements 301 to 30n.

The detection device 300 is manufactured by the steps shown in FIG. 8. In this case, covers 1 to 3 should be replaced with covers 311 to 313, respectively, and antennas 9, 11 and 12 should be replaced with antennas 110, 120 and 130, respectively.

In step S1, n groups each composed of recesses 101, 102, 104 and 105 and n groups each composed of through-holes 103 and 106 are formed in the cover 311. In step S2, n sets of through-holes 201, 203 to 206 are formed in the cover 312.

In step S3, n oscillators 4 are formed. In step S4, the n oscillators 4 are disposed in the n recesses 102. In step S5, the cover 312 is brought into contact with the cover 311 such that the n sets of through-holes 201, 203 to 206 face the n sets of recesses 102, 104 and 105 and n sets of through-holes 103 and 106, and the cover 312 is joined to the cover 311 using anodic bonding.

In step S6, the cover 313 is disposed in contact with the side of the cover 312 opposite the side thereof that is in contact with the cover 311, and the cover 313 is joined to the cover 312 using anodic bonding.

In step S7, the antennas 110 and 120 are disposed on the top surface 311A of the cover 311 above the n oscillators 4 contained in the n elements 301 to 30$n$, and the antenna 130 is disposed on the bottom surface 313A of the cover 313 below the n oscillators 4 contained in the n elements 301 to 30$n$. This results in a completed detection device 300.

A specific example A of the detection device 300 is a detection device 300 plus a cover 140. In this case, the n elements 301 to 30$n$ are connected in series by the cover 140. The n oscillators 4 contained in the n elements 301 to 30$n$ have the same thickness.

The specific example A of the detection device 300 detects material to be detected in the same manner as that for the detection device 100A discussed above, and can be used semipermanently.

A specific example B of the detection device 300 is a detection device 300 plus a cover 160. In this case, the n oscillators 4 contained in the n elements 301 to 30$n$ have the same thickness or different thicknesses.

The specific example B of the detection device 300 detects material to be detected in the same manner as that for the detection device 100E discussed above, and can be used semipermanently.

Thus, either the cover 140 or the cover 160 may be added to the detection device 100 or detection device 300 to connect the n testing spaces 13 in series or in parallel.

As a result, the detection device 100 or 300 is capable of detecting one or n types of material to be detected in one or n types of liquid.

In the detection device 100 or 300, the n oscillators 4 are not pinched by the covers 1 to 3 or covers 311 to 313, similar to the detection device 10 such that they vibrate freely when an electromagnetic field is applied.

Thus, stable vibration of the oscillators 4 can be ensured in the detection device 100 or 300, too.

Figure 18:
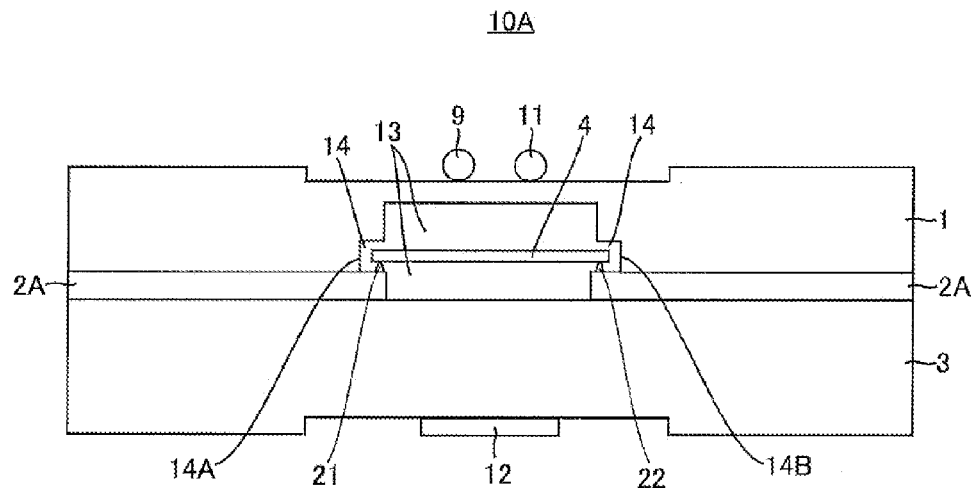
FIG. 18 is a cross-sectional view of still another detection device according to an embodiment of the present invention.
Figure 19:
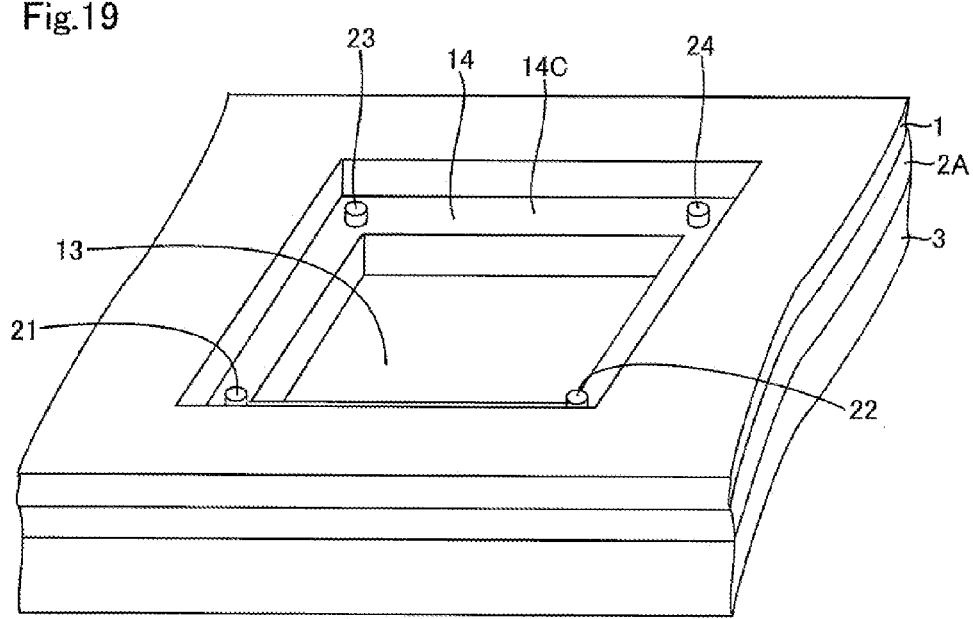
FIG. 19 is an enlarged view of the testing space and minute space shown in FIG. 18.

FIG. 18 is a cross-sectional view of still another detection device according to an embodiment of the present invention. FIG. 19 is an enlarged view of the testing space 13 and minute space 14 shown in FIG. 18. Note that FIG. 19 shows only portions of the cover 1 that constitute the sidewalls 14A and 14B of the minute space 14 in the cover 1 forming the testing space 13 and the minute space 14.

The detection device according to an embodiment of the present invention may be the detection device 10A shown in FIGS. 18 and 19. Referring to FIGS. 18 and 19, in the detection device 10A, the cover 2 of the detection device 10 shown in FIGS. 1 to 3 is replaced by a cover 2A, and is otherwise the same as the detection device 10.

The cover 2A is disposed between the cover 1 and the cover 3, in contact with both covers 1 and 3. The cover 2A is made of the same material as the cover 2.

In the detection device 10A, the height H3 of the minute space 14 is in the range of 70 to 80 µm. As a result, in the detection device 10A, the height H1 of the testing space 13 is in the range of 170 to 180 µm.

The cover 2A is a cover 2 shown in FIG. 2 plus projections 21 to 24, and otherwise the same as the cover 2.

Each of the projections 21 to 24 is columnar, for example, and has a diameter of 50 µm φ and a height of 50 µm. The projections 21 to 24 are disposed on the bottom surface 14C of the minute space 14. In this case, the projections 21 to 24 are positioned at the four vertices of a rectangle that is similar to the rectangle of the testing space 13. The cover 2A is formed integrally with the projections 21 to 24.

In the detection device 10A, the oscillator 4 is placed on the projections 21 to 24. As a result, in the detection device 10A, the oscillator 4 is only in contact with the four projections 21 to 24 in its edge portions, making the contact area between the oscillator 4 and the cover 2A of the detection device 10A smaller than that between the oscillator 4 and the cover 2 of the detection device 10 such that the oscillator 4 vibrates more freely than in the detection device 10. Thus, free vibration of the oscillator can be ensured.

Further, the projections 21 to 24 support the oscillator 4 horizontally. As a result, when material to be detected is to be detected while liquid to be tested is circulated, the liquid to be tested can flow smoothly in the testing space 13. Thus, material to be detected can be accurately detected while liquid to be tested is circulated.

Each of the projections 21 to 24 may have an end (i.e. a contact with the oscillator 4) that is hemispheric, or may be pointed in the shape of a triangular pyramid or rectangular pyramid, for example. If each of the projections 21 to 24 has an end that is hemispheric or is painted in the shape of a triangular pyramid or rectangular pyramid, for example, the oscillator 4 is in point contact with the projections 21 to 24, further reducing the contact area between the oscillator 4 and the projections 21 to 24. As a result, the oscillator 4 vibrates still more freely. Thus, free vibration of the oscillator can be ensured.

Figure 20:
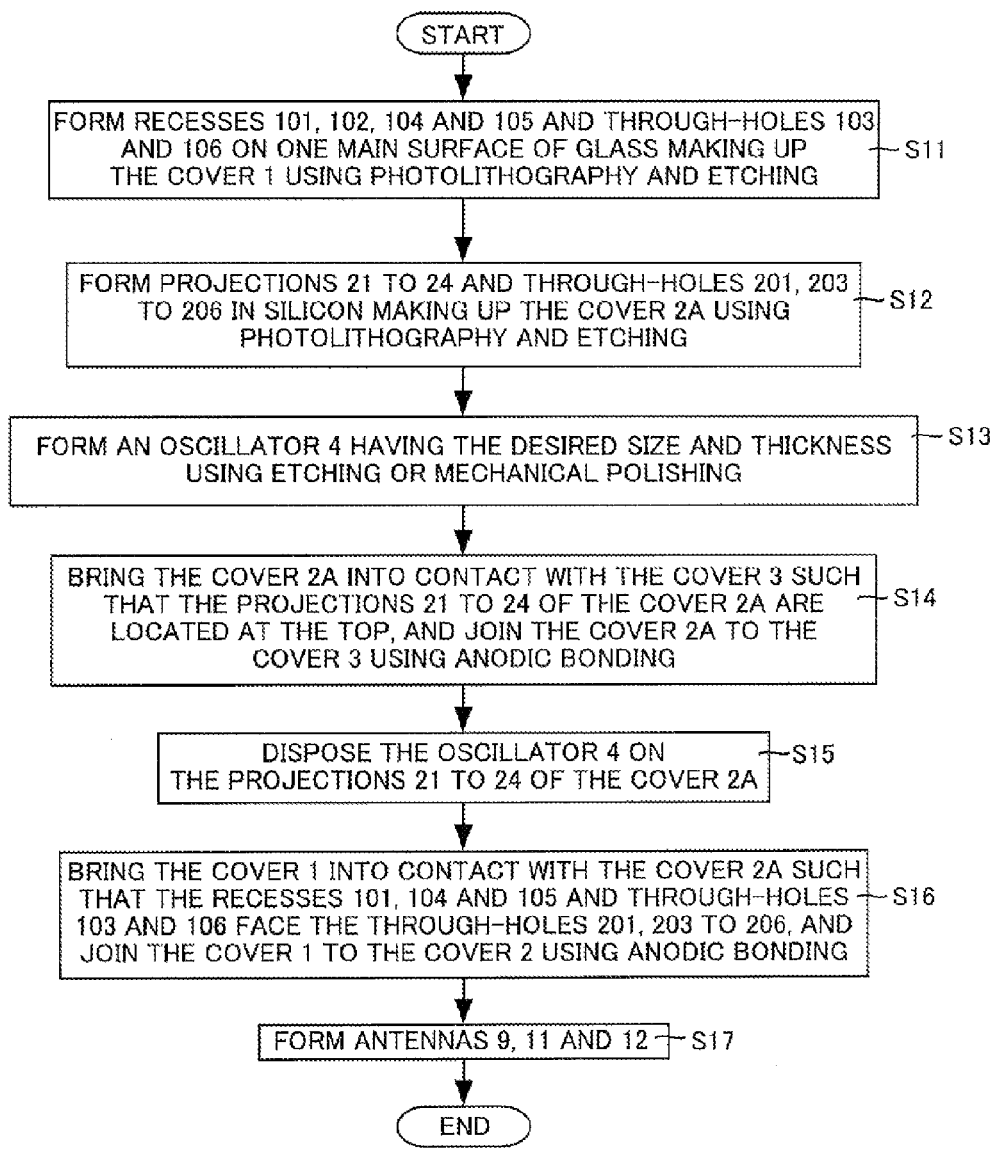
FIG. 20 is a process chart illustrating a method of manufacturing a detection device as shown in FIGS. 18 and 19.

FIG. 20 is a process chart illustrating a method of manufacturing a detection device 10A as shown in FIGS. 18 and 19. Referring to FIG. 20, after manufacture of a detection device 10A is initiated, recesses 101, 102, 104 and 105 and through-holes 103 and 106 are formed on one main surface of glass making up the cover 1 using photolithography and etching as in semiconductor technology (step S11). In this case, the recesses 101, 102, 104 and 105 and through-holes 103 and 106 have different depths, and thus application of resist and patterning and etching of resist are repeated to make shallower structures before deeper ones, and thus the recesses 101, 102, 104 and 105 and through-holes 103 and 106 are formed.

Thereafter, projections 21 to 24 and through-holes 201, 203 to 206 are formed in silicon making up the cover 2A using photolithography and etching (step S12). In this case, application of resist and patterning and etching of resist are repeated to form projections 21 to 24 and then form through-holes 201, 203 to 206.

Then, an oscillator 4 having the desired size and thickness is formed using etching and mechanical polishing (step S13).

Subsequently, the cover 2A is brought into contact with the cover 3 such that the projections 21 to 24 on the cover 2A are located at the top, and the cover 2A is joined to the cover 3 using anodic bonding, as discussed above (step S14).

Then, the oscillator 4 is placed on the projections 21 to 24 on the cover 2A (step S15).

Then, the cover 1 is brought into contact with the cover 2A such that the recesses 101 and 104 and through-holes 103 and 106 of the cover 1 face the through-holes 201, 203 to 206 of the cover 2A before the cover 1 is joined to the cover 2A using anodic bonding, as discussed above (step S16). Thus, an inlet port 5, inlet path 6, outlet path 7 and outlet port 8 and minute space 14 are formed.

Then, antennas 9, 11 and 12 are formed (step S17). This results in a completed detection device 10.

Figure 21:
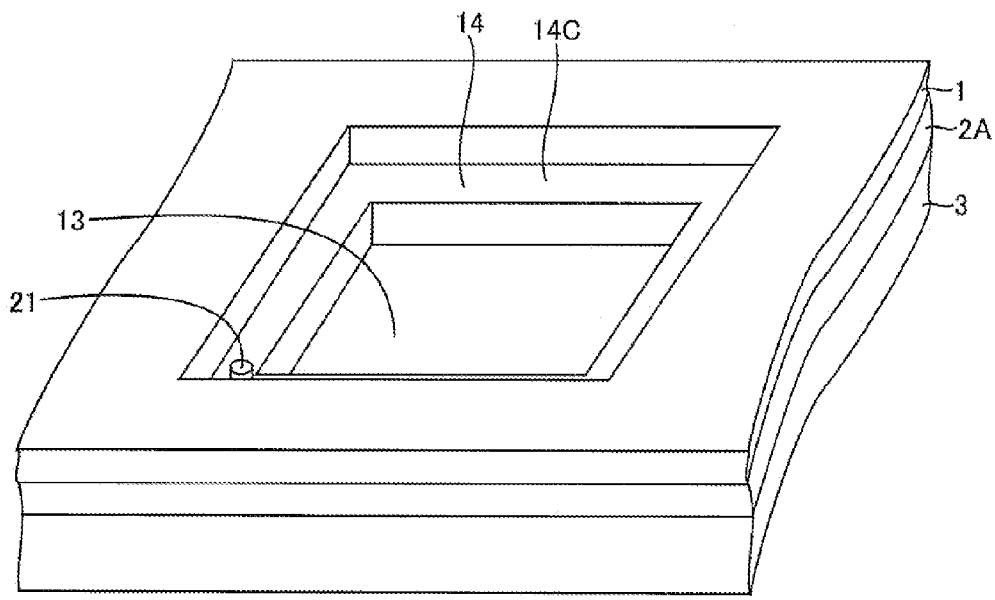
FIG. 21 is another enlarged view of a testing space and minute space as shown in FIG. 18.

FIG. 21 is another enlarged view of the testing space 13 and minute space 14 shown in FIG. 18. FIG. 21, too, shows only those portions of the cover 1 forming the testing space 13 and minute space 14 that constitute the sidewalls 14A and 14B of the minute space 14.

In the detection device 10A, the cover 2A may only have one projection 21. The oscillator 4 is disposed in the testing space 13 and minute space 14 on the projection 21 in one of its edge portions. As a result, the contact area between the oscillator 4 and the bottom surface 14C of the minute space 14 is smaller than is the case if there is no projection 21 such that the oscillator 4 vibrates more freely than is the case if there is no projection 21. Thus, free vibration of the oscillator 4 can be ensured.

Figure 22:
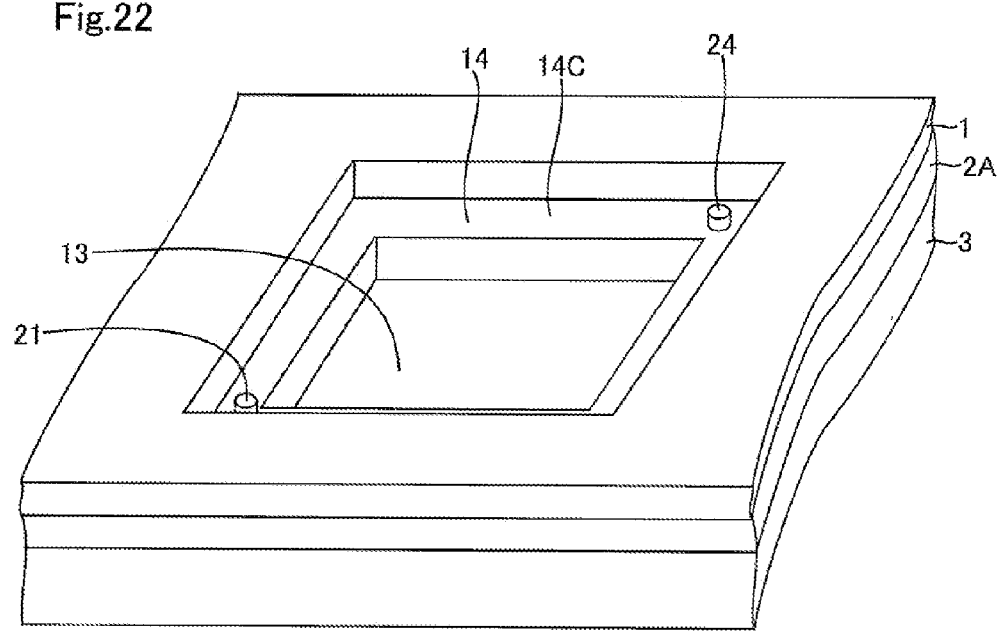
FIG. 22 is still another enlarged view of a testing space and minute space as shown in FIG. 18.

FIG. 22 is yet another enlarged view of the testing space 13 and minute space 14 shown in FIG. 18. FIG. 22, too, shows only those portions of the cover 1 forming the testing space 13 and minute space 14 that constitute the sidewalls 14A and 14B of the minute space 14.

In the detection device 10A, the cover 2A may have two projections 21 and 24. The oscillator 4 is disposed in the testing space 13 and minute space 14 on the two projections 21 and 24 in some of its edge portions. As a result, the contact area between the oscillator 4 and the bottom surface 14C of the minute space 14 is smaller than is the case if there are no projections 21 and 24 such that the oscillator 4 vibrates more freely than is the case if there are no projections 21 and 24. Thus, free vibration of the oscillator 4 can be ensured.

It should be noted that the cover 2A may have other pairs of projections than the pair of projections 21 and 24, such as a pair of projections 21 and 22, a pair of projections 22 and 23, a pair of projections 21 and 23, a pair of projections 22 and 24 or a pair of projections 23 and 24. In this case, the contact area between the oscillator 4 and the bottom surface 14C of the minute space 14 is smaller such that the oscillator 4 vibrates more freely than is the case if there are no projections 21 and 22 or the like. Thus, free vibration of the oscillator 4 can be ensured.

If the cover 2A has two projections, the two projections may be disposed in other locations and with other distances than those shown in FIG. 22, i.e. may be disposed in any locations and with any distance on the bottom surface 14C of the minute space 14.

Figure 23:
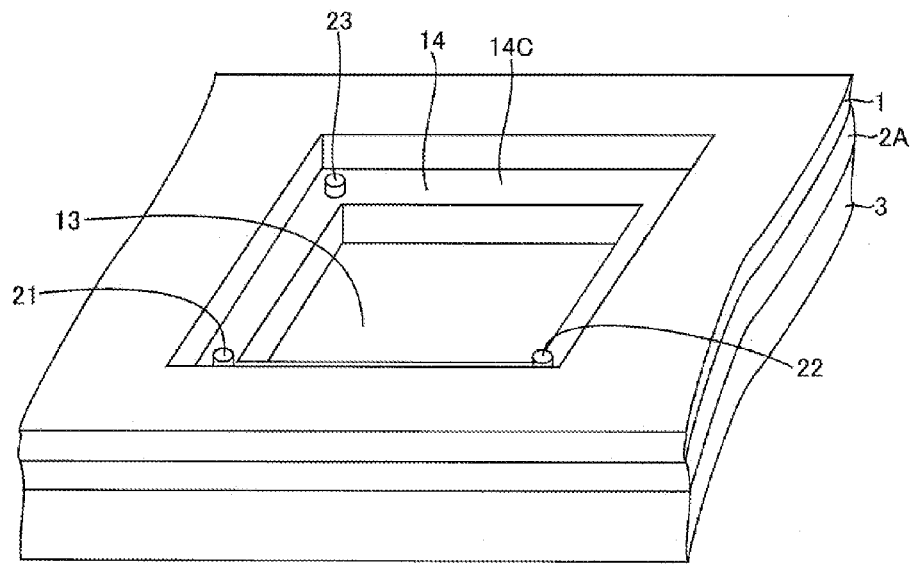
FIG. 23 is further another enlarged view of a testing space and minute space as shown in FIG. 18.

FIG. 23 is still another enlarged view of the testing space 13 and minute space 14 shown in FIG. 18. FIG. 23, too, shows only those portions of the cover 1 forming the testing space 13 and minute space 14 that constitute the sidewalls 14A and 14B of the minute space 14.

In the detection device 10A, the cover 2A may have three projections 21 to 23. In such an implementation, the oscillator 4 is disposed in the testing space 13 and minute space 14 on the three projections 21 to 23 in some of its edge portions. As a result, the contact area between the oscillator 4 and the bottom surface 14C of the minute space 14 is smaller than is the case if there are no projections 21 to 23 such that the oscillator 4 vibrates more freely than is the case if there are no projection 21 to 23. Thus, free vibration of the oscillator 4 can be ensured.

It should be noted that the cover 2A may have other sets of three projections than the set of projections 21 to 23, such as a set of three projections 22 to 24, a set of three projections 21, 22 and 24 or a set of three projections 21, 23 and 24. In this case, the contact area between the oscillator 4 and the bottom surface 14C of the minute space 14 is smaller such that the oscillator 4 vibrates more freely than is the case if there are no projections 22 to 24 or the like. Thus, free vibration of the oscillator 4 can be ensured.

If the cover 2A has three projections, the three projections may be disposed in other locations and with other distances than those shown in FIG. 23, i.e. may be disposed in any locations and with any distances on the bottom surface 14C of the minute space 14.

It should be noted that in the detection device 10A, the cover 2A may have five or more projections and may generally have m (in is a positive integer) projections. If the cover 2A has three or more projections, the three or more projections are capable of supporting the oscillator 4 horizontally.

Figure 24:
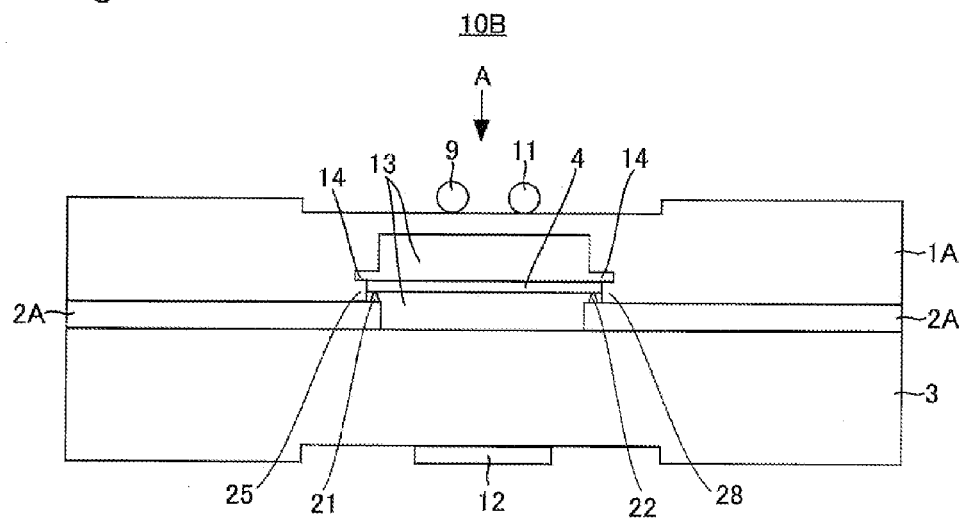
FIG. 24 is a cross-sectional view of still another detection device according to an embodiment of the present invention.
Figure 25:
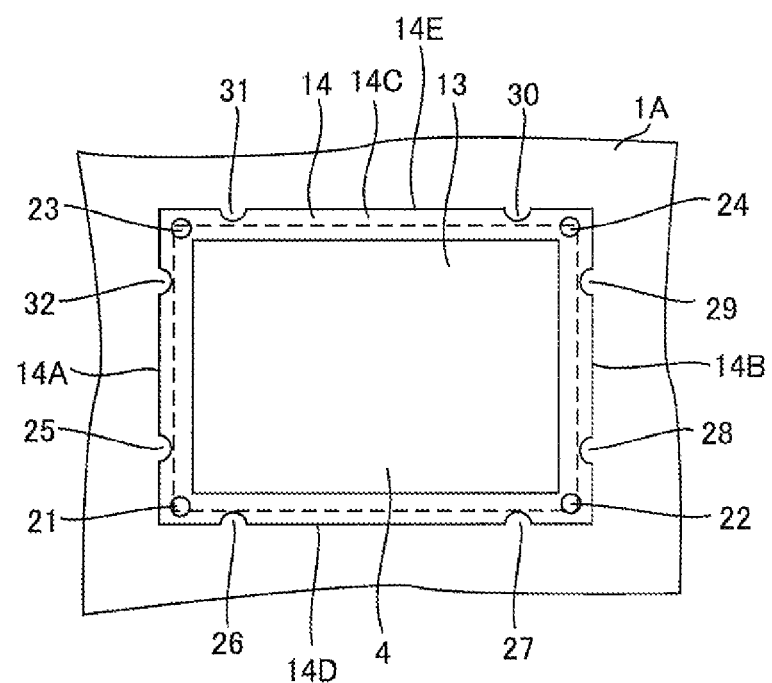
FIG. 25 is a plan view of the testing space and minute space viewed in the direction of A shown in FIG. 24.

FIG. 24 is a schematic view of yet another detection device according to an embodiment of the present invention. FIG. 25 is a plan view of the testing space 13 and minute space 14 viewed in the direction of A shown in FIG. 24. FIG. 25 only shows those portions of the cover 1A forming the testing space 13 and minute space 14 that constitute the sidewalls 14A and 14B of the minute space 14.

The detection device according to an embodiment of the present invention may be the detection device 10B shown in FIGS. 24 and 25. Referring to FIGS. 24 and 25, in the detection device 10B, the cover 1 of the detection device 10A shown in FIGS. 18 to 19 is replaced by a cover 1A, and is otherwise the same as the detection device 10A.

The cover 1A is in contact with the cover 2A and is joined to the cover 2A. The cover 1A is made of the same material as the cover 1 set forth above.

The cover 1A is a cover 1, as set forth above, plus support members 25 to 32, and is otherwise the same as the cover 1.

The support members 25 to 32 are provided on the sidewalls 14A, 14B, 14D and 14E of the minute space 14 to protrude from the minute space 14 into the testing space 13. More specifically, the support members 25 and 32 are provided on the sidewall 14A of the minute space 14, the support members 26 and 27 are provided on the sidewall 14D of the minute space 14, the support members 28 and 29 are provided on the sidewall 14B of the minute space 14, and the support members 30 and 31 are provided on the sidewall 14E of the minute space 14. Each of the support members 25 to 32 is provided close to one of the four angles of the testing space 13.

Each of the support members 25 to 32 has a semicircular cross section. The cover 1A is integrally formed with the support members 25 to 32.

The oscillator 4 (indicated by the dotted lines in FIG. 25) is disposed such that its edge portions are located on the projections 21 to 24 and its edges are in contact with the support members 25 to 32. In this case, the oscillator 4 is in point contact with the support members 25 to 32.

As a result, the contact area between the oscillator 4 and the covers 1A and 2A is smaller than that between the oscillator 4 and the cover 2 of the detection device 10 such that the oscillator 4 vibrates more freely than in the detection device 10. Thus, free vibration of the oscillator 4 can be ensured.

The oscillator 4 is supported by the support members 25 to 32 in directions parallel to the planes of the covers 1A, 2A and 3. As a result, the oscillator 4 is less likely to move in a direction parallel to the planes of the covers 1A, 2A and 3 even when liquid to be tested is circulated in the testing space 13 and minute space 14. Thus, material to be detected can be accurately detected even when liquid to be tested is circulated.

In the detection device 10B, the support members 25 to 32 may be disposed in other locations than close to the four angles of the testing space 13, i.e. in any locations on the sidewalls 14A, 14B, 14D and 14E of the minute space 14 with any distance.

Figure 26:
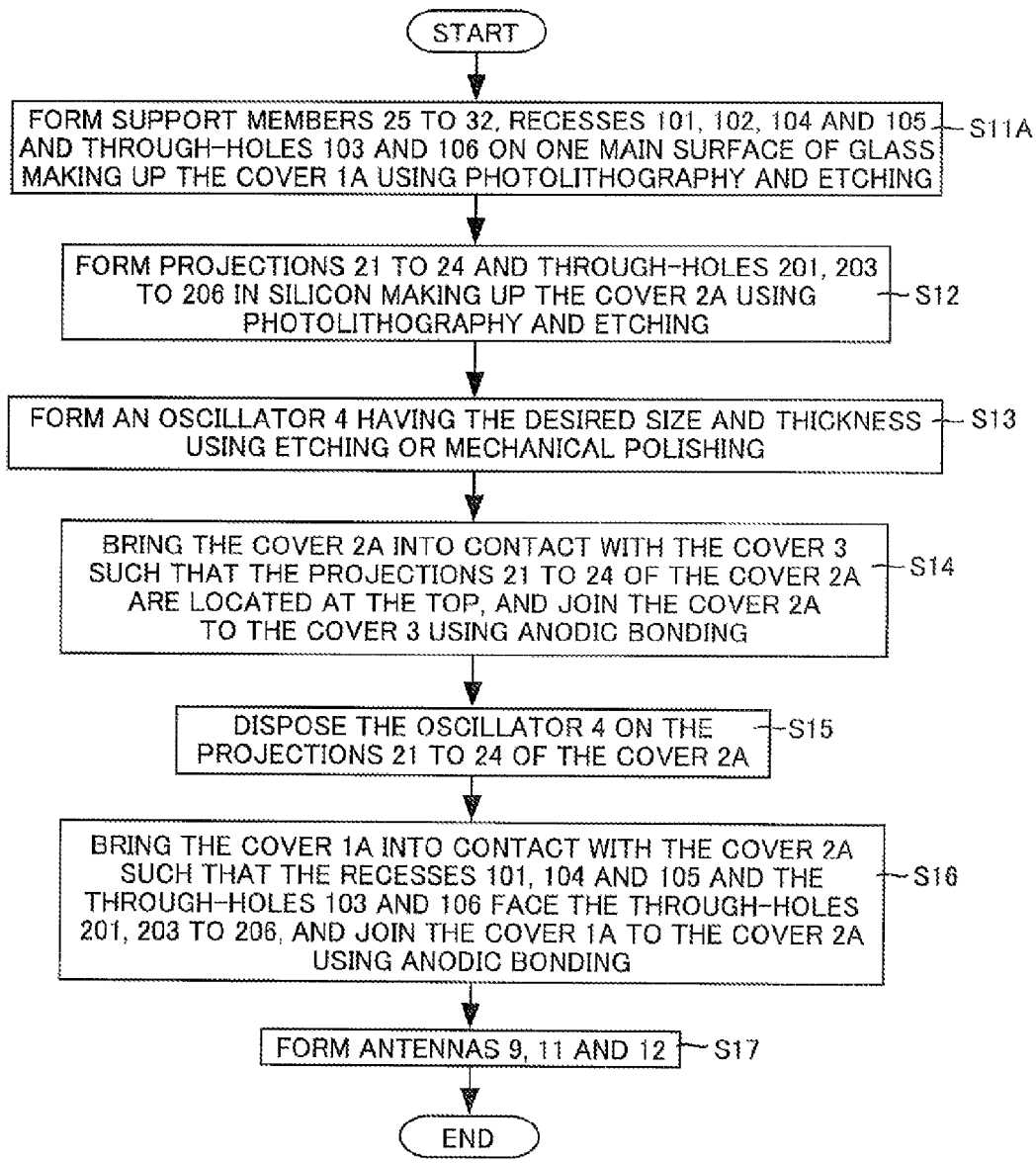
FIG. 26 is a process chart illustrating a method of manufacturing a detection device as shown in FIGS. 24 and 25.

FIG. 26 is a process chart illustrating a method of manufacturing a detection device 10B as shown in FIGS. 24 and 25. In the process chart shown in FIG. 26, step S11 of the process chart shown in FIG. 20 is replaced by step S11A, and the other steps are the same as in the process chart shown in FIG. 20.

Referring to FIG. 26, after manufacture of a detection device 10B is initiated, support members 25 to 32, recesses 101, 102, 104 and 105 and through-holes 103 and 106 are formed on one main surface of glass making up the cover 1A using photolithography and etching as in semiconductor technology (step S11A). In this case, the support members 25 to 32, recesses 101, 102, 104 and 105 and through-holes 103 and 106 have different depths, and thus application of resist and patterning and etching of resist are repeated to make shallower structures before deeper ones, and thus the support members 25 to 32, recesses 101, 102, 104 and 105 and through-holes 103 and 106 are formed. If support, members 25 to 32 are to be formed, resist is patterned using a mask having such a pattern as formed by the sidewalls 14A, 19B, 14D and 14E of the minute space 14 shown in FIG. 25.

After step S11A, steps S12 to S17 discussed above are performed in the stated order to produce a completed detection device 10B.

In the detection device 10B, too, the cover 2A may have m projections, as set forth above. The in projections may be disposed in any locations and with any distance(s).

If liquid to be tested flows from the sidewall 14A of the minute space 14 toward the sidewall 14B, the cover 1A may only have support members 27 to 30 out of the support members 25 to 32, and if liquid to be tested flows from the sidewall 14B of the minute space 14 toward the sidewall 14A, the cover 1A may only have support members 25, 26, 31 and 32 out of the support members 25 to 32. The oscillator 4 is unlikely to move if support members are provided downstream as liquid to be tested flows through the testing space 13.

The other parts of the detection device 10B can be described similarly to the detection device 10A.

Figure 27:
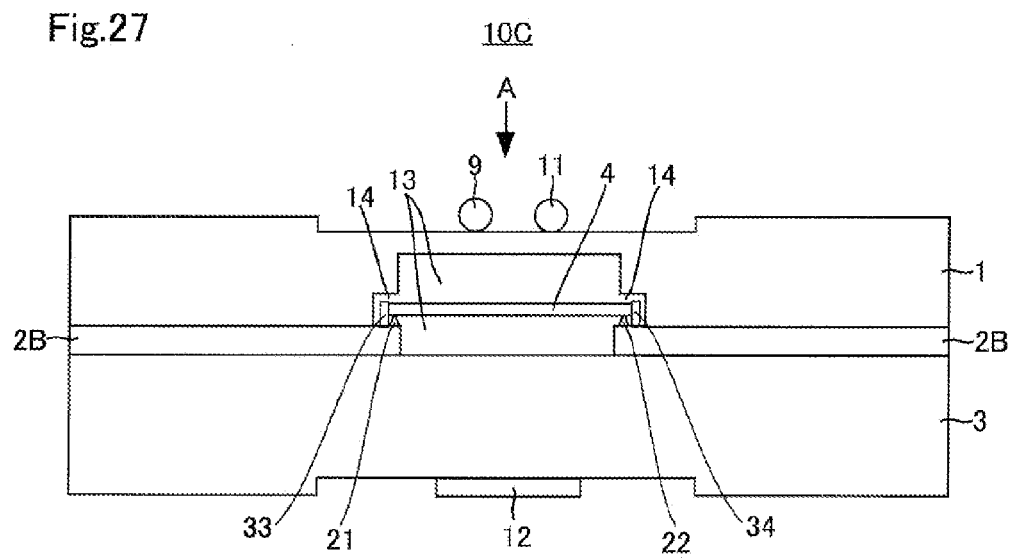
FIG. 27 is a cross-sectional view of still another detection device according to an embodiment of the present invention.
Figure 28:
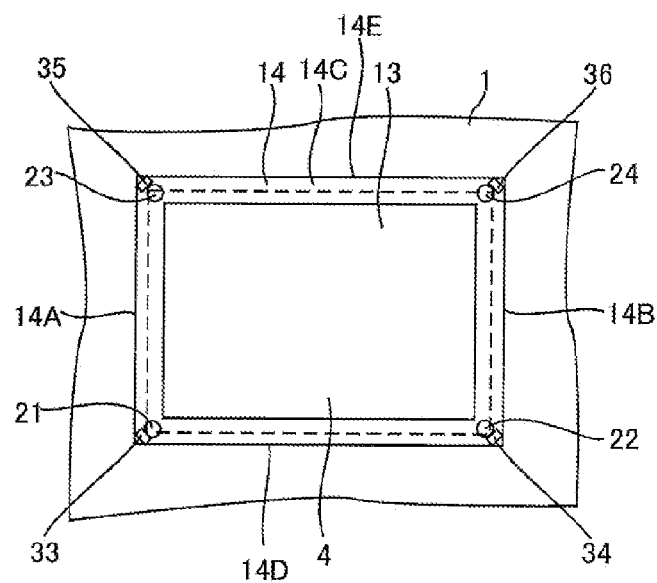
FIG. 28 is a plan view of the testing space and minute space viewed in the direction of A shown in FIG. 27.

FIG. 27 is a cross-sectional view of yet another detection device according to an embodiment of the present invention. FIG. 28 is a plan view of the testing space 13 and minute space 14 viewed in the direction of A shown in FIG. 27. FIG. 28 only shows those portions of the cover 2B forming the testing space 13 and minute space 14 that constitute the sidewalls 14A and 14B of the minute space 14.

The detection device according to an embodiment of the present invention may be the detection device 10C shown in FIGS. 27 and 28. Referring to FIGS. 27 and 28, in the detection device 10C, the cover 2A of the detection device 10A shown in FIG. 18 is replaced by a cover 2B, and is otherwise the same as the detection device 10A.

The cover 2B is disposed between the cover 1 and the cover 3 in contact with both covers 1 and 3. The cover 2B is made of the same material as the cover 2 as described above.

The cover 2B is a cover 2A, as set forth above, plus support members 33 to 36, and is otherwise the same as the cover 2A.

The support members 33 to 36 are provided on the bottom surface 14C of the minute space 14, each closer to a corner of the minute space 14 than their respective one of the projections 21 to 24 is. More specifically, the support member 33 is provided closer to a corner of the minute space 14 than the projection 21 is, the support member 34 is provided closer to a corner of the minute space 14 than the projection 22 is, the support member 35 is provided closer to a corner of the minute space 14 than the projection 23 is, and the support member 36 is provided closer to a corner of the minute space 14 than the projection 24 is.

Each of the support members 33 to 36 has a rectangular cross section. The cover 2B is formed integrally with the projections 21 to 24 and support members 33 to 36.

The oscillator 4 (indicated by the dotted lines in FIG. 28) is disposed such that its edge members are located on the projections 21 to 24 and its four vertices are in contact with the support members 33 to 36. In this implementation, the oscillator 4 is in point contact with the support members 33 to 36.

As a result, the contact area between the oscillator 4 and the cover 2B is smaller than that between the oscillator 4 and the cover 2 of the detection device 10 such that the oscillator 4 vibrates more freely than in the detection device 10. Thus, free vibration of the oscillator 4 can be ensured.

The oscillator 4 is supported by the support members 33 to 36 in directions parallel to the planes of the covers 1, 2B and 3. As a result, the oscillator 4 is unlikely to move in a direction parallel to the planes of the covers 1, 2B and 3 even when liquid to be tested is circulated through the testing space 13 and minute space 14. Thus, material to be detected can be accurately detected even when liquid to be tested is circulated.

Figure 29:
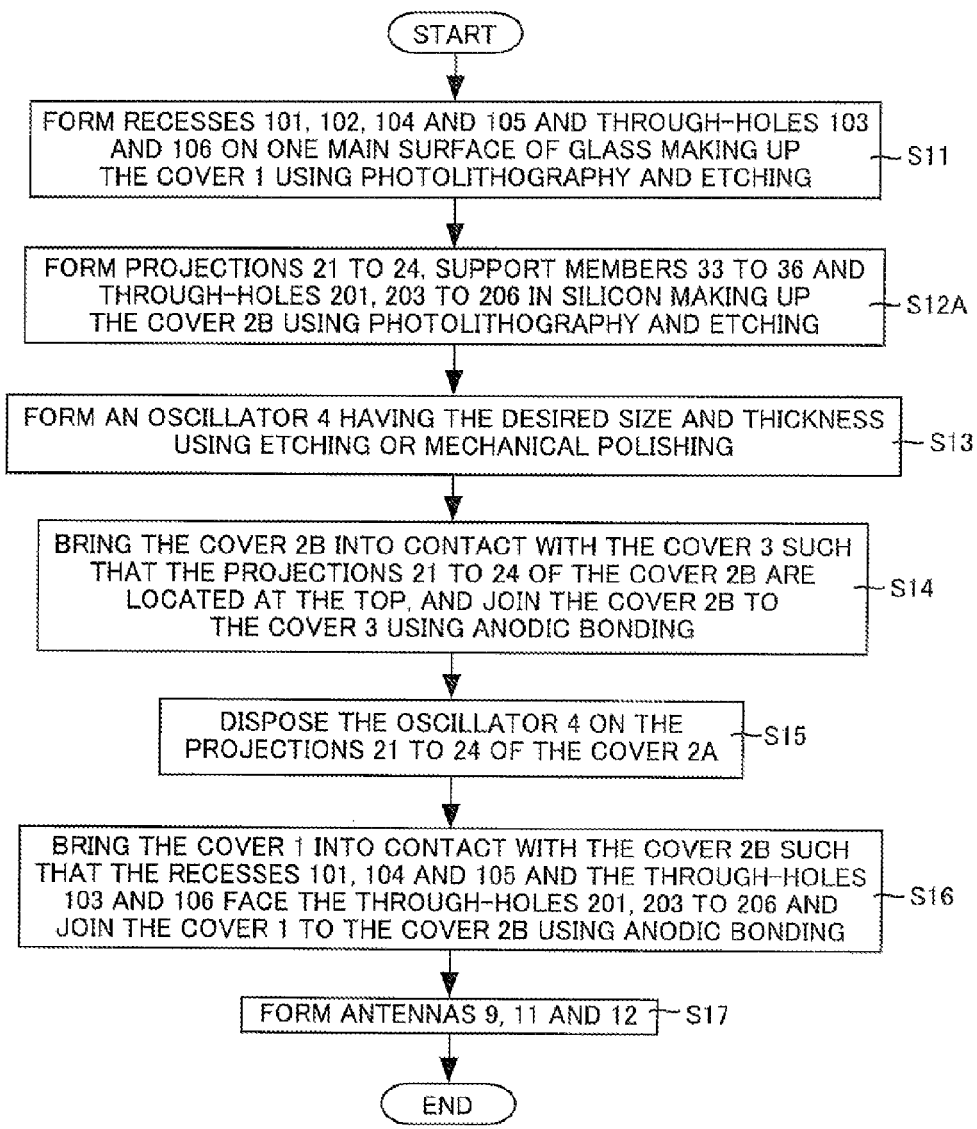
FIG. 29 is a process chart illustrating a method of manufacturing a detection device as shown in FIGS. 27 and 28.

FIG. 29 is a process chart illustrating a method of manufacturing a detection device 10C as shown in FIGS. 27 and 28. In the process chart shown in FIG. 29, step S12 of the process chart shown in FIG. 20 is replaced by step S12A, and the other steps are the same as in the process chart shown in FIG. 20.

Referring to FIG. 29, after manufacture of a detection device 10C is initiated, step S11 described above is performed to fabricate the cover 1. Then, projections 21 to 24, support members 33 to 36 and through-holes 201, 203 to 206 are formed in silicon making up the cover 2B using photolithography and etching (step S12A). Thus, the cover 2b is fabricated.

Then, steps S13 to S17 discussed above are performed in the stated order to produce a completed detection device 10C.

It should be noted that in the detection device 10C, too, the cover 2B may have m projections, as discussed above. The m projections may be disposed in any locations and with any distance(s).

If liquid to be tested flows from the sidewall 14A of the minute space 14 toward the sidewall 14B, the cover 2B may only have support members 34 and 36 out of the support members 33 to 36, and if liquid to be tested flows from the sidewall 14B of the minute space 14 toward the sidewall 14A, the cover 1A may only have support members 33 and 35 out of the support members 33 to 36. The oscillator 4 is unlikely to move if support members are provided downstream as liquid to be tested flows through the testing space 13.

The other parts of the detection device 10C can be described similarly to the detection device 10A.

Figure 30:
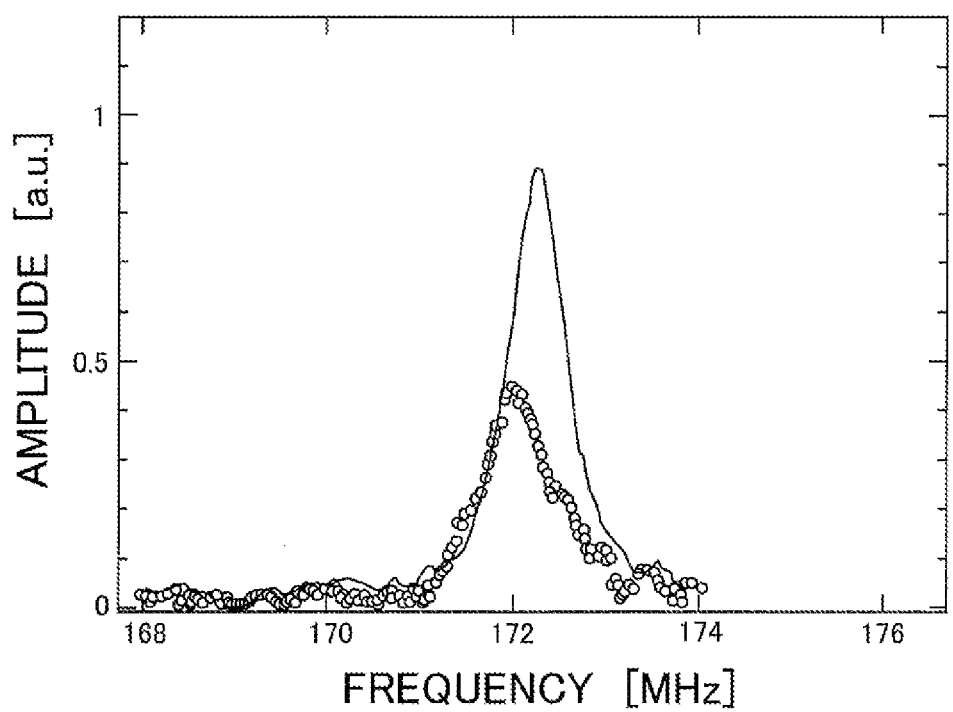
FIG. 30 is a graph showing the results of vibration tests of an oscillator.

FIG. 30 is a graph showing the results of vibration tests of an oscillator 4. In FIG. 30, the vertical axis represents amplitude and the horizontal axis represents frequency. The solid line indicates the results of vibration tests of the oscillator 4 in the detection device 10A and the series of circles indicates the results of vibration tests of the oscillator 4 as pinched along its periphery.

Referring to FIG. 30, when the oscillator 4 was not pinched, amplitudes of vibration were significantly larger than is the case when the oscillator 4 was pinched along its periphery.

Thus, it has been proved by an experiment that free vibration of the oscillator 4 can be ensured in the detection device 10A.

Figure 31:
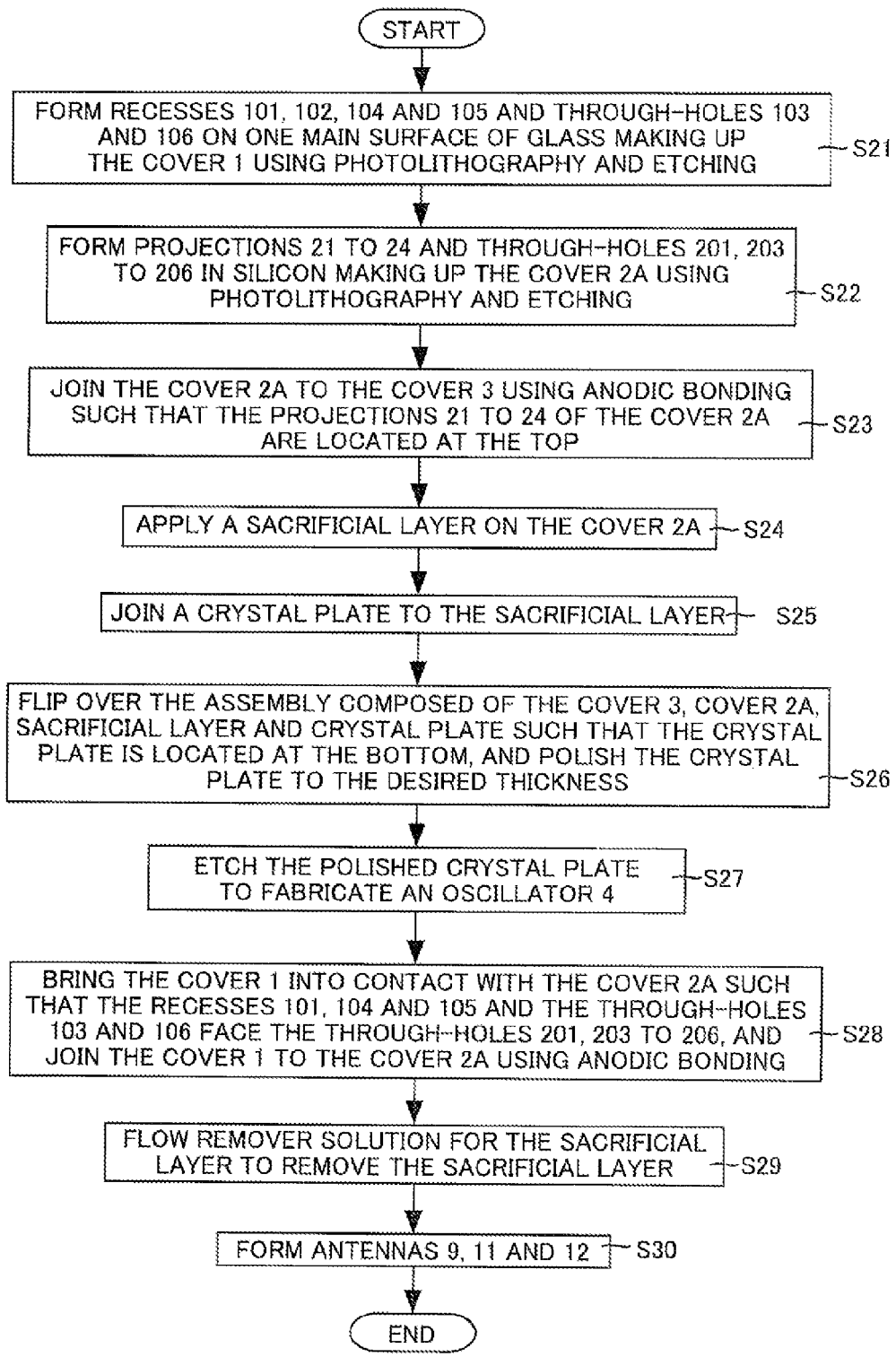
FIG. 31 is a process chart illustrating another method of manufacturing a detection device as shown in FIGS. 18 and 19.

FIG. 31 is a process chart illustrating another method of manufacturing a detection device 10A as shown in FIGS. 18 and 19. Referring to FIG. 31, after manufacture of a detection device 10A is initiated, recesses 101, 102, 104 and 105 and through-holes 103 and 106 are formed on one main surface of glass making up the cover 1 using photolithography and etching as in semiconductor technology (step S21). In this case, the recesses 101, 102, 104 and 105 and through-holes 103 and 106 have different depths, and thus application of resist and patterning and etching of resist are repeated to make shallower structures before deeper ones, and thus the recesses 101, 102, 104 and 105 and through-holes 103 and 106 are formed.

Thereafter, projections 21 to 24 and through-holes 201, 203 to 206 are formed in silicon making up the cover 2A using photolithography and etching (step S22). In this case, application of resist and patterning and etching of resist are repeated to form projections 21 to 24 before forming through-holes 201 and 203 to 206.

Then, the cover 2A is joined to the cover 3 using anodic bonding such that the projections 21 to 24 of the cover 2A are located at the top (step S23).

Subsequently, a sacrificial layer is applied to the cover 2A (step S24). The sacrificial layer is made of a polyimide called HD-3007 (HD Micro Systems), for example.

Thereafter, a crystal plate is joined to the sacrificial layer (step S25). Then, the assembly composed of the cover 3, cover 2A, sacrificial layer, and crystal plate is flipped over such that the crystal plate is located at the bottom, and the crystal plate is polished to the desired thickness (step S26). Subsequently, the polished crystal plate is etched to fabricate an oscillator 4 (step S27).

Then, the cover 1 is brought into contact with the cover 2A such that the recesses 101 and 104 and through-holes 103 and 106 of the cover 1 face the through-holes 201 and 203 to 206 of the cover 2A, and the cover 1 is joined to the cover 2A using anodic bonding as discussed above (step S28). Thus, an inlet port 5, inlet path 6, outlet path 7, outlet port 8 and testing space 13 are formed.

Then, the sacrificial layer is removed by flowing a remover solution for the sacrificial layer into the testing space 13 through the formed inlet port 5, inlet path 6, outlet path 7 and outlet port 8 (step S29). Thus, a minute space 14 is formed and the edge portions of the oscillator 4 are in contact with the projections 21 to 24 in the minute space 14. The remover solution for the sacrificial layer is made of EKC865 (Dupont EKC Technology), for example.

Then, antennas 9, 11 and 12 are formed (step S30). This results in a completed detection device 10A.

It should be noted that steps S24 and S25 described above may be replaced by the steps of applying a sacrificial layer to a crystal plate and joining the crystal plate to the cover 2A using the applied sacrificial layer.

Thus, in the process chart of FIG. 31, an assembly composed of a cover 3, cover 2A, sacrificial layer and crystal plate is formed before the crystal plate is polished to the desired thickness (see step S26) such that the thickness of the oscillator 4 may be made smaller than is the case when a crystal plate is polished to fabricate an oscillator 4. As a result, the sensitivity for detecting material to be detected can be improved.

It should be noted that the detection devices 10, 10B and 10C discussed above may also be manufactured in accordance with the process chart of FIG. 31. Further, the detection devices 100, 100A, 100B and 300 may also be manufactured in accordance with the process chart of FIG. 31.

Figure 32:
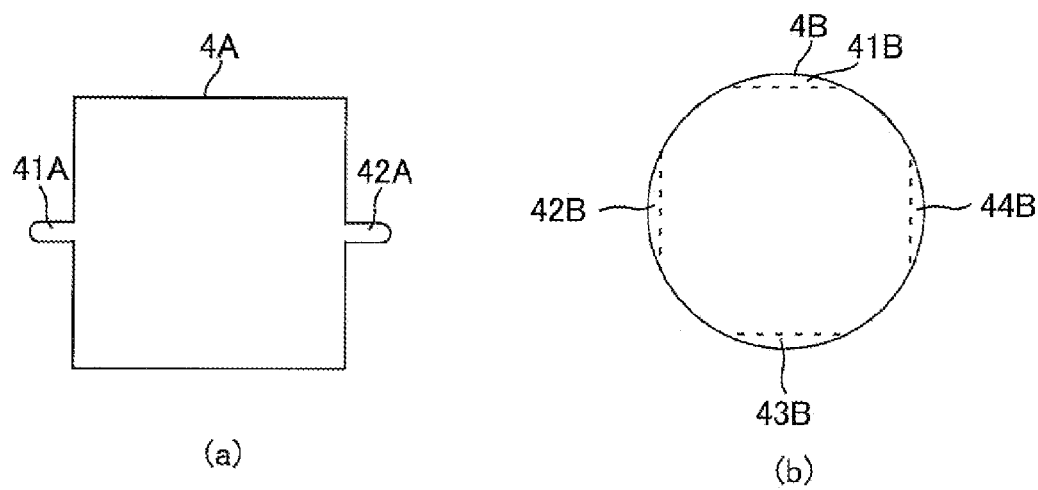
FIG. 32 illustrates other oscillators.

FIG. 32 illustrates other oscillators. The oscillator 4 may be the oscillator 4A (see (a) of FIG. 32). The oscillator 4A has a generally rectangular shape and has projections 41A and 42A. The projections 41A and 42A are positioned on two opposite sides of the rectangle. The two projections 41A and 42A of the oscillator 4A are inserted into the minute space 14.

If the oscillator 4A is used, only the projections 41A and 42A of the oscillator 4A are in contact with the cover 2 or 312, resulting in more stable vibration than with the oscillator 4.

It should be noted that the oscillator 4A may have projections on the four sides of the rectangle.

The oscillator 4 may be the oscillator 4B (see (b) of FIG. 32). The oscillator 4B has a generally circular shape. Out of four edge portions 41B, 42B, 43B and 44B in two perpendicular diametrical directions, at least two opposite edge portions 41B and 43B (or 42B and 44B) may be inserted into the minute space 14.

The oscillator 4 may have other polygonal shapes than those shown in FIG. 32, such as triangular, rectangular, pentagonal, and heptagonal shapes. If the oscillator 4 is polygonal, two opposite edge portions of the oscillator 4 are at least inserted into the minute space 14.

In embodiments of the present invention, the antennas 9 and 11 may be located below the cover 3, and the antenna 12 may be located above the cover 1.

Also, in embodiments of the present invention, all of the antennas 9, 11 and 12 may be located close to one side of the oscillator 4. In such implementations, the antennas 9, 11 and 12 are arranged, close to one side of the oscillator 4, in the order of the antennas 9, 12 and 11 toward one direction on one plane.

Further, in embodiments of the present invention, the antennas 110 and 120 may be located below the unit elements 91 to 9n and the antenna 130 may be located above the unit elements 91 to 9n.

Further, in embodiments of the present invention, all of the antennas 110, 120 and 130 may be located on one side of the unit elements 91 to 9n. In such implementations, the antennas 110, 120 and 130 are arranged, on one side of the unit elements 91 to 9n, in the order of the antennas 110, 130 and 120 toward one direction on one plane.

Further, in embodiments of the present invention, the antennas 110 and 120 may be located on the bottom surface 313A of the cover 313 and the antenna 130 may be located on the top surface 311A of the cover 311.

Further, in embodiments of the present invention, all of the antennas 110, 120 and 130 may be located on one of the bottom surface 313A of the cover 313 and the top surface 311A of the cover 311. In such implementations, the antennas 110, 120 and 130 are arranged, on one of the bottom surface 313A of the cover 313 and the top surface 311A of the cover 311, in the order of the antennas 110, 130 and 120 toward one direction on one plane.

Further, in the above description, the covers 2 and 312 are made of silicon. However, embodiments of the present invention are not limited thereto and the covers 2 and 312 may be made of glass. In such implementations, the cover 2 is joined to the covers 1 and 3 using either diffusion bonding or heating/pressurizing bonding. The cover 312 is joined to the covers 311 and 313 using either diffusion bonding or heating/pressurizing bonding.

Further, in embodiments of the present invention, the detection device 10 may include an inlet path 6 only composed of an inlet path 6b. Each of the unit elements 91 to 9n may include an inlet path 6 only composed of an inlet path 6b. In such implementations, the other end of the inlet path 6b is connected to the inlet port 5.

Further, in embodiments of the present invention, each of the unit elements 91 to 9n of the detection device 100, 100A or 100B may be fabricated using the covers 1, 2A and 3, oscillator 4, inlet port 5, inlet path 6, outlet path 7, outlet port 8, testing space 13 and minute space 14 of the detection device 10A; each of the unit elements 91 to 9n of the detection device 100, 100A or 100B may be fabricated using the covers 1A, 2A and 3, oscillator 4, inlet port 5, inlet path 6, outlet path 7, outlet port 8, testing space 13 and minute space 14 of the detection device 10B; or each of the unit elements 91 to 9n of the detection device 100, 100A or 100B may be fabricated using the covers 1, 2B and 3, oscillator 4, inlet port 5, inlet path 6, outlet path 7, outlet port 8, testing space 13 and minute space 14 of the detection device 10C.

Further, in embodiments of the present invention, the detection device 300 may be fabricated with one of the detection devices 10A, 10B and 10C.

Further, since it has been proved by an experiment that the oscillator 4 vibrates sufficiently in air, the detection devices 10, 10A, 10B, 10C, 100, 100A, 100B and 300 may be used as gas sensors.

Further, since in the detection device 10C two support members (the support members 34 and 36 or the support members 33 and 35) are sufficient on the cover 2B, the cover of a detection device according to embodiments of the present invention may have k (k is an integer not smaller than 2) support members.

Further, in embodiments of the present invention, the antenna 12 or antenna 130 constitutes the "first antenna", the antenna 9 or antenna 110 constitutes the "second antenna", and the antenna 11 or antenna 120 constitutes the "third antenna".

Further, in embodiments of the present invention, the cover 1 constitutes the "first cover", the cover 2 constitutes the "second cover", and the cover 3 constitutes the "third cover".

Further, in embodiments of the present invention, the cover 140 or cover 160 constitutes the "auxiliary cover".

The embodiment disclosed herein should be understood as being in every respect exemplary and not restrictive. The scope of the present invention is indicated by the claims and not by the above description of embodiments, and is intended to include all the modifications encompassed within the spirit and scope equivalent to those of the claims.

INDUSTRIAL APPLICABILITY

The present invention may be employed in a detection device using an oscillator.

The invention claimed is:

1. A detection device comprising:
a cover including, in its interior, a testing space into which liquid to be tested is introduced, and a minute space that is open to the testing space;
an inlet path provided in the cover and introducing the liquid into the testing space;
an outlet path provided in the cover and discharging the liquid from the testing space;
an oscillator disposed in the testing space, and having a size that is larger than that of the testing space and having an edge portion inserted into the minute space;
a first antenna connected to a ground potential;
a second antenna working together with the first antenna to apply an electromagnetic field to the oscillator; and
a third antenna working together with the first antenna to receive, from the oscillator, a reception signal composed of a vibration signal produced while the oscillator vibrates.

2. The detection device according to claim 1, wherein the cover includes:
a first cover including, on one main surface, a first recess having a generally U-shaped cross section and a second recess continuing from an edge of the first recess and having a generally L-shaped cross section;
a second cover including a through-hole having substantially the same size as the first recess, the through-hole facing the first recess and a portion of the second cover other than the through-hole being in contact with the one main surface of the first cover to form the minute space; and
a third cover disposed in contact with a side of the second cover that is opposite a side in contact with the first cover and forming the testing space together with the first recess and the through-hole.

3. The detection device according to claim 2, wherein the first and third covers are made of glass, and the second cover is made of silicon.

4. The detection device according to claim 1, wherein the cover further includes at least one projection formed on a bottom surface of the minute space below the edge portion of the oscillator inserted into the minute space, and
the edge portion of the oscillator is disposed on the at least one projection.

5. The detection device according to claim 4, wherein the at least one projection includes three or more projections that support the oscillator generally horizontally.

6. The detection device according to claim 5, wherein the cover further includes at least two support members that supporting a portion of a side of the oscillator.

7. A detection device comprising:
a cover including, in its interior, a plurality of testing spaces into which liquid to be tested is introduced, and a plurality of minute spaces provided to correspond to the plurality of testing spaces and being open to their corresponding testing spaces;
a plurality of inlet paths provided in the cover to correspond to the plurality of testing spaces and introducing the liquid into their corresponding testing spaces;
a plurality of outlet paths provided in the cover to correspond to the plurality of testing spaces and discharging the liquid from their corresponding testing spaces;
a plurality of oscillators provided to correspond to the plurality of testing spaces, each oscillator being disposed in its respective testing space and having a size larger than that of the testing space and having an edge portion inserted into its respective minute space;
a first antenna connected to a ground potential;
a second antenna working together with the first antenna to apply an electromagnetic field to the plurality of oscillators; and
a third antenna working together with the first antenna to receive, from the plurality of oscillators, a reception signal composed of a vibration signal produced while each oscillator vibrates.

8. The detection device according to claim 7, further comprising an auxiliary cover disposed in contact with the cover and having a plurality of auxiliary paths,
wherein each of the plurality of auxiliary paths connects one of the outlet paths provided to correspond to one of two adjacent testing spaces with one of the inlet paths provided to correspond to the other of the two testing spaces.

9. The detection device according to claim 7, further comprising an auxiliary cover disposed in contact with the cover and having a plurality of auxiliary paths provided to correspond to the plurality of testing spaces,
   wherein each of the plurality of auxiliary paths is composed of a first auxiliary path introducing the liquid from an outside into one of the inlet paths provided to correspond to its respective testing space and a second auxiliary path discharging to the outside the liquid from one of the outlet paths provided to correspond to its respective testing space.

10. The detection device according to claim 7, wherein the plurality of oscillators have a generally identical thickness.

11. The detection device according to claim 7, wherein the plurality of oscillators have different thicknesses.

12. A detection device comprising:
a plurality of unit elements;
a first antenna connected to a ground potential;
a second antenna working together with the first antenna to apply an electromagnetic field to a plurality of oscillators contained in the plurality of unit elements; and
a third antenna working together with the first antenna to receive, from the plurality of oscillators, a reception signal composed of a vibration signal produced while each oscillator vibrates,
wherein each of the plurality of unit elements includes:
a cover including, in its interior, a testing space into which liquid to be tested is introduced and a minute space that is opened to the testing space;
an inlet path provided in the cover and introducing the liquid into the testing space;
an outlet path provided in the cover and discharging the liquid from the testing space; and
an oscillator disposed in the testing space and having a size larger than that of the testing space and having an edge portion inserted into the minute space.

13. The detection device according to claim 12, further comprising an auxiliary cover disposed in contact with a plurality of the covers included in the plurality of unit elements and including a plurality of auxiliary paths that each connects two adjacent testing spaces of the plurality of testing spaces contained in the plurality of unit elements,
   wherein each of the plurality of auxiliary paths connects the outlet path provided to correspond to one of the two such testing spaces with the inlet path provided to correspond to the other one of the two testing spaces.

14. The detection device according to claim 13, further comprising an auxiliary cover disposed in contact with a plurality of the covers included in the plurality of unit elements and including a plurality of auxiliary paths provided to correspond to a plurality of the testing spaces contained in the plurality of unit elements,
   wherein each of the plurality of auxiliary paths is composed of a first auxiliary path introducing the liquid from an outside into the inlet path provided to correspond to its respective testing space and a second auxiliary path discharging the liquid to the outside from the outlet path provided to correspond to its respective testing space.

* * * * *